United States Patent
Nozato et al.

(10) Patent No.: US 9,875,541 B2
(45) Date of Patent: Jan. 23, 2018

(54) ENHANCED ALGORITHM FOR THE DETECTION OF EYE MOTION FROM FUNDUS IMAGES

(71) Applicants: CANON KABUSHIKI KAISHA, Tokyo (JP); University of Rochester, Rochester, NY (US)

(72) Inventors: Koji Nozato, Rochester, NY (US); Kenichi Saito, Yokohama (JP); Qiang Yang, Rochester, NY (US)

(73) Assignees: Canon Kabushiki Kaisha, Tokyo (JP); University of Rochester, Rochester, NY (US)

( * ) Notice: Subject to any disclaimer, the term of this patent is extended or adjusted under 35 U.S.C. 154(b) by 192 days.

(21) Appl. No.: 14/996,111

(22) Filed: Jan. 14, 2016

(65) Prior Publication Data
US 2017/0206657 A1    Jul. 20, 2017

(51) Int. Cl.
*G06T 7/00* (2017.01)
*A61B 3/00* (2006.01)
*A61B 3/14* (2006.01)
*G06K 9/00* (2006.01)
*G06K 9/62* (2006.01)
*G06T 7/20* (2017.01)

(52) U.S. Cl.
CPC .......... *G06T 7/0016* (2013.01); *A61B 3/0025* (2013.01); *A61B 3/14* (2013.01); *G06K 9/0061* (2013.01); *G06K 9/00335* (2013.01); *G06K 9/6201* (2013.01); *G06T 7/004* (2013.01); *G06T 7/20* (2013.01); *G06T 2207/30041* (2013.01); *G06T 2207/30196* (2013.01)

(58) Field of Classification Search
CPC ......... G06T 7/0016; G06T 7/004; G06T 7/20; G06K 9/0061; G06K 9/00335; G06K 9/6201; A61B 3/0025; A61B 3/14
See application file for complete search history.

(56) References Cited

U.S. PATENT DOCUMENTS

| 5,784,148 | A  | 7/1998 | Heacock |
| 6,337,920 | B1 | 1/2002 | Muhlhoff |
| 6,379,006 | B1 | 4/2002 | Eikelboom et al. |

(Continued)

OTHER PUBLICATIONS

Scott B. Stevenson, Austin Roorda, Correcting for Miniature Eye Movements in High Resolution Scanning Laser Ophthalmoscopy, 2005, authors manuscript, <URL:http://roorda.vision.berkeley.edu/Pubs/StevensonRoordaSPIE5688.pdf>, Berkeley, CA.

(Continued)

*Primary Examiner* — Neil Mikeska
(74) *Attorney, Agent, or Firm* — Canon U.S.A., Inc. I.P. Division

(57) ABSTRACT

A method, controller, and non-transitory medium for obtaining images of a moving subject. Estimating changes in position of the subject based on the images. Calculating a quality metric of the estimation of the change. Comparing the quality metric to a threshold. In a first case in which the quality metric is less than the threshold, adjusting position of the scanning area based on the estimated change in position. In a second case in which the quality metric is not less than the threshold, obtaining a new second image.

20 Claims, 14 Drawing Sheets

(56) References Cited

U.S. PATENT DOCUMENTS

| | | | |
|---|---|---|---|
| 7,031,501 B2 * | 4/2006 | Adachi | G06K 9/00087 |
| | | | 382/124 |
| 7,118,216 B2 | 10/2006 | Roorda | |
| 7,374,287 B2 | 5/2008 | Van de Velde | |
| 7,404,640 B2 | 7/2008 | Ferguson et al. | |
| 7,515,734 B2 | 4/2009 | Horovitz et al. | |
| 7,665,844 B2 | 2/2010 | Chen et al. | |
| 7,805,009 B2 | 9/2010 | Everett et al. | |
| 7,970,170 B2 * | 6/2011 | Tener | G06T 3/4038 |
| | | | 382/103 |
| 8,444,268 B2 | 5/2013 | Hammer et al. | |
| 8,770,751 B2 | 7/2014 | Ferguson et al. | |
| 9,226,656 B2 * | 1/2016 | Yang | A61B 3/1025 |
| 2010/0253908 A1 | 10/2010 | Hammer et al. | |
| 2012/0072121 A1 * | 3/2012 | Mollicone | A61B 5/0022 |
| | | | 702/19 |
| 2012/0293610 A1 * | 11/2012 | Doepke | H04N 5/23238 |
| | | | 348/36 |
| 2013/0242261 A1 | 9/2013 | Ohishi et al. | |
| 2014/0104618 A1 | 4/2014 | Potsaid et al. | |
| 2014/0218498 A1 | 8/2014 | Sato | |

OTHER PUBLICATIONS

Stephen aA Burns, Remy Tumbar, Ann E. Elsner, Daniel Ferguson, Daniel X. Hammer, Large-Field-of-View, Modular, Stabilized, Adaptive-Optics-Based Scanning Laser Ophthalmoscope, 2007 Authors manuscript.

* cited by examiner 804-c1

804-c2

ENHANCED ALGORITHM FOR THE DETECTION OF EYE MOTION FROM FUNDUS IMAGES

GOVERNMENT LICENSE RIGHTS

This invention was made with government support under grant numbers EY014375 and EY001319 awarded by the National Institutes of Health. The Government has certain rights in the invention.

BACKGROUND

Field of Art

The present disclosure relates to a system and method for controlling an opthalmoscope.

Description of the Related Art

Ophthalmoscopes, ophthalmic image pickup apparatuses, fundus imaging systems such as: scanning laser ophthalmoscopes (SLOs) that irradiate the fundus with a laser in two dimensions; and optical coherence tomographs (OCTs) that utilizes the interference of low coherence light have been developed and commercialized. Thus, SLOs and OCTs have become important tools for the study of the human fundus in both normal and diseased eyes. Eye movement is a big issue for these imaging devices.

For example, a SLO may take multiple images for averaging and constructing panoramic images. For constructing these panoramic images, each image should be at a precise position. This can be difficult to accomplish because the eye moves continuously during imaging. Especially, on small FOV (Field of View) system such as AO-SLO (Adaptive Optics SLO) eye movement is quite large when compared with the image size of the images and sometimes the imaging area can go out of frame easily due to eye movement.

The robustness of the typical eye tracking process may run into difficulties due to incorrect detection of eye motion when dealing with low contrast images from a diseased eye. Images of a diseased eye are often accompanied by high noise due to low reflection from the diseased areas. This issue is exacerbated by uncertainty of the peak location from cross correlation calculations when random noise negatively disturbs image features, and/or image features and image background do not provide sufficient information for the cross correlation. Unsuccessful tracking becomes worse particularly when the reference image and the target image (image to be correlated) have long temporal interval where parameters such as amount of torsion, brightness/contrast, and noise level of retinal images keeps changing.

What is needed is an eye position tracking system that is both fast and robust. The applicants have developed a process that addresses this problem. The process detects the eye position in a robust manner with a position detection system and shifts imaging area according to the eye movement with tracking mirrors.

SUMMARY

An aspect of an embodiment is a method of imaging a scanning area of a subject by scanning imaging light over periods of time on the scanning area of the subject. The method may include constructing a plurality of images based on detection of the imaging light from the scanning area of the subject, each image among the plurality of images obtained during a different time period. The plurality of images may include at least: a reference image, a first image, and a second image. The first image may be obtained during a first period of time, the second image may be obtained during a second period of time, the reference image may be obtained during a third period of time that is prior to the first period of time and the second period of time. The method may include estimating a first relative change in position of the scanning area of the subject by comparing the reference image and the first image. The method may include estimating a second relative change in position of the scanning area of the subject by comparing the reference image and the second image. The method may include estimating a third relative change in position of the scanning area of the subject by comparing the first image and the second image. The method may include calculating a quality metric of estimation of the second relative change in position based on: the first relative change in position; the second relative change in position; the third relative change in position. The method may include comparing the quality metric to a threshold. In a first case in which the quality metric is less than the threshold, the method may include adjusting position of the scanning area based on the second relative change in position. In a second case in which the quality metric is not less than the threshold, the method may include obtaining a new second image during a new second period of time.

In an alternative embodiment the method may include, in the second case, the position of the scanning area may be controlled based upon previous image position information.

In an alternative embodiment the method may include, the second image may be an image of the scanning area of the subject that is obtained immediately after the first image is obtained.

In an alternative embodiment, in the first case the method may include setting the second image as a new first image; setting the second relative change in position as a new first relative change in position; obtaining the new second image during the new second period of time, wherein the new second image is an image of the scanning area of the subject that is obtained immediately after the new first image is obtained; estimating a new second relative change in position of the scanning area of the subject by comparing the reference image and the new second image; estimating a new third relative change in position of the scanning area of the subject by comparing the new first image and the new second image; calculating a new quality metric of estimation of the new second relative change in position based on: the new first relative change in position; the new second relative change in position; the new third relative change in position; and comparing the new quality metric to the threshold, in the first case wherein the new quality metric is less than the threshold, adjusting position of the scanning area based on the new second relative change in position; and in the second case wherein the new quality metric is greater than the threshold, reobtaining the new second image during a reset new second period of time.

In an alternative embodiment the method may include performing pre-processing on each of the plurality of images before estimating relative changes in position; wherein the pre-processing is changed according to status of imaging. In an alternative embodiment, the pre-processing may include applying either a smoothing filter or a Sobel filter according to status of imaging. In an alternative embodiment, the status of imaging may be an average intensity of an image among the plurality of images to the pre-processing is to be applied. In an alternative embodiment, the status of imaging may be a size of the scanning area. In an alternative embodiment, the status of imaging may be a focusing position of the imaging light. In an alternative embodiment, the pre-processing may include dividing each of the plurality of images into smaller images, the estimating of relative changes in position is performed on the smaller images, and adjusting the position of the scanning area, are all done during periods of time in which each undivided image is being obtained.

In an alternative embodiment, the method may further comprise: calculating a second quality metric based on a magnitude of the second relative change in position; comparing the second quality metric to a second threshold, in a third case wherein the second quality metric is less than the second threshold, adjusting position of the scanning area based on the second relative change in position; and in a second case wherein the second quality metric is not less than the second threshold, not adjusting the position of the scanning area.

In an alternative embodiment, the method may further comprise: obtaining a plurality of potential reference images; and setting the reference image as an average of the plurality of potential reference images.

In an alternative embodiment, the method may further comprise: obtaining a plurality of potential reference images; and setting one of the plurality of potential reference images as the reference image based on imaging conditions of each of the plurality of potential reference images.

In an alternative embodiment, the imaging condition may be an average intensity of each of the plurality of potential reference images.

In an alternative embodiment, the imaging condition may be a similarity between a first potential reference image and a second potential reference image obtained immediately prior to obtaining the first potential reference image.

In an alternative embodiment, in the first case, the second image may be used to construct a larger image by stitching the second image together with other images, and in the second case, the second image is not used to construct the larger image.

In an alternative embodiment, in the first case, the second image may be used to create a video image by using the second image together with other images to form a time series, and in the second case, the second image is not used to construct the video image.

In an alternative embodiment, first image and the second image may be among a time series of images of the scanning area of the subject. The second image may be the next image after the first image in the time series of images of the scanning area of the subject.

An alternative embodiment, may be a non-transitory computer readable medium encoded with instructions for a processor to perform the method of an embodiment.

An alternative embodiment, may be a controller including memory and a processor. The control may perform the method of an embodiment.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Figure 1A:
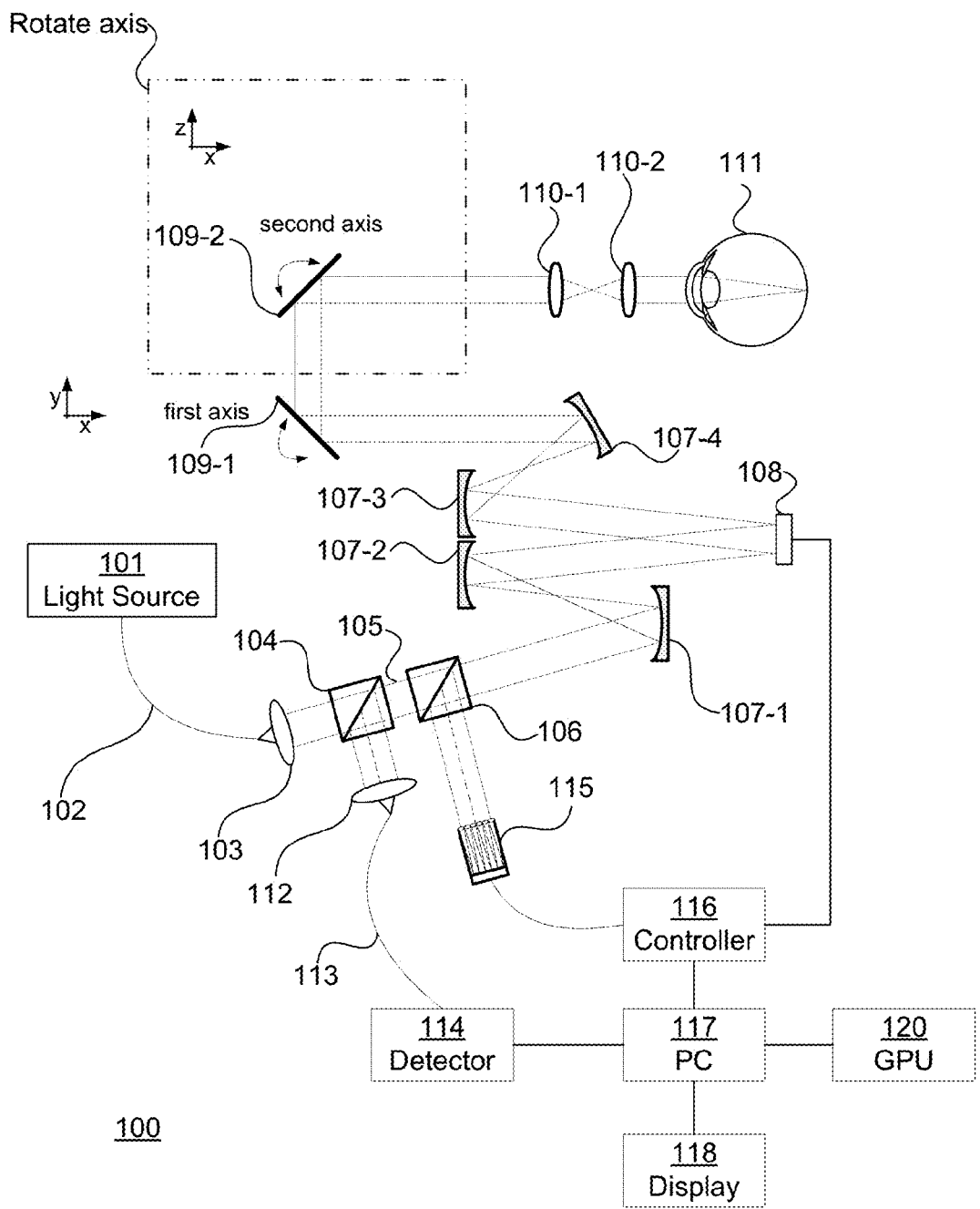
FIGS. 1A-B are illustrations of ophthalmoscopes in which embodiments may be implemented.

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following which is used to inspect an eye as described below may also be used to inspect other objects including but not limited to skin, and internal organs.

Ophthalmoscope 1

A first embodiment is described with reference to a fundus image photographing apparatus (opthalmoscope) such as the photographing apparatus illustrated in FIG. 1A.

Embodiments are directed towards systems, methods, non-transitory computer readable medium, and software which are used in connection with an imaging system such as an opthalmoscope 100. FIG. 1A is an illustration of an exemplary opthalmoscope 100. An opthalmoscope 100 is a system or apparatus for obtaining information about an interior portion of the eye 111 (e.g., the fundus).

An exemplary embodiment may be a scanning opthalmoscope. A scanning opthalmoscope scans a spot across the eye 111. The spot may be a spot of light from a light source 101 that is scanned across the eye 111.

In an exemplary embodiment 100, the spot of light is produced by a light source 101. The light source 101 may be incorporated into the opthalmoscope 100; alternatively, the opthalmoscope 100 may include an input for receiving the light source 101. The input for the light source 101 may be a fiber optic input or a free space input. The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare perceived by a person being inspected while maintaining imaging resolution.

In an exemplary embodiment, light emitted from the light source 101 passes through a single-mode optical fiber 102, and is radiated as collimated light (measuring light 105) by a collimator 103.

In an exemplary embodiment, the polarization of the irradiated light may be adjusted by a polarization adjusting member 119 (not shown) provided in a path of the single-mode optical fiber 102. In an alternative configuration, the light source 101 is polarized and single-mode optical fiber 102 is polarization maintaining fiber. In another configuration, the polarization adjusting member may be placed after the collimator 103. Alternatively, the polarization adjusting member may be replaced with a polarizer. In an alternative embodiment, the irradiated light may be unpolarized, depolarized, or the polarization may be uncontrolled.

The measuring light 105 radiated from the collimator 103 passes through a light division portion 104 including a beam splitter. An exemplary embodiment includes an adaptive optical system.

The adaptive optical system may include a light division portion 106, a wavefront sensor 115, wavefront adjustment device 108, and reflective mirrors 107-1 to 107-4 for guiding the measuring light 105 to and from those components. The reflective mirrors 107-1 to 107-4 are provided to guide the measuring light 105 to and from the pupil of an eye 111, the wavefront sensor 115, and the wavefront adjustment device 108. The reflective mirrors may be replaced with suitable optics, such as lenses and/or apertures. The wavefront sensor 115 and the wavefront adjustment device 108 may be in an optically conjugate relationship. A beam splitter may be used as the light division portion 106. The wavefront sensor 115 may be a Shack-Hartmann sensor or other type of sensor that gathers information that is representative of the wavefront of light coming from the subject.

The measuring light 105 passing through the light division portion 106 is reflected by the reflective mirrors 107-1 and 107-2 so as to enter the wavefront adjustment device 108. The measuring light 105 is reflected by the wavefront adjustment device 108 and is further reflected by the reflective mirrors 107-3 and 107-4.

The wavefront adjustment device 108 maybe a transmissive device or a reflective device. The wavefront adjustment device 108, may be an addressable spatial light phase modulator that allows relative phases across a beam coming into the wavefront adjustment device 108 to be adjusted such that relative phases across the beam coming out of the wavefront adjustment device 108 are adjustable. In an exemplary embodiment, one or two spatial phase modulators including a liquid crystal element is used as the wavefront adjustment device 108. The liquid crystal element may modulate a phase of only a specific polarized component. In which case, two liquid crystal elements may be employed to modulate substantially orthogonal polarized components of the measuring light 105. In an alternative embodiment, the wavefront adjustment device 108 is a deformable mirror.

The measuring light 105 reflected off mirror 107-4 is two-dimensionally scanned by a scanning optical system 109. In an exemplary embodiment, the scanning optical system 109 includes a first scanner 109-1 and a second scanner 109-2. The first scanner 109-1 rotates around the first axis, while the second scanner 109-2 rotates around a second axis. The first axis is substantially orthogonal to the second axis. Substantially in the context of the present disclosure means within the alignment and measurement tolerances of the system.

FIG. 1A illustrates the first scanner 109-1 rotating in the x-y plane, while the second scanner 109-2 is rotating in the z-x plane. In the context of the present disclosure, rotating the measuring light 105 in a first plane around the first axis is equivalent to rotating the measuring light 105 in the first plane and is equivalent to scanning the spot of light in the main scanning direction or the lateral direction of the object being imaged. In the context of the present disclosure, rotating the measuring light 105 in a second plane around the second axis is equivalent to scanning the spot of light in the sub-scanning direction or the longitudinal direction of the object being imaged. The sub-scanning direction is substantially orthogonal to the main scanning direction.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single tip-tilt mirror that is rotated around the first axis and around the second axis that is substantially orthogonal to the first axis. An exemplary embodiment may also use non-mechanical beam steering techniques.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency. There may be additional optical components, such as lenses, mirrors, apertures, and etc. between the scanners 109-1, 109-2, and other optical components. These additional optical components may be arranged such that the light is focused onto the scanners, in a manner that is optically conjugate with all of or one or more of the subject 111, the wavefront adjustment device 108, the wavefront sensor 115, and a detector 114.

The measuring light 105 scanned by the scanning optical system 109 is radiated to the eye 111 through eyepieces 110-1 and 110-2. The measuring light radiated to the eye 111 is reflected, scattered, or absorbed on the fundus 111. When the eyepieces 110-1 and 110-2 are adjusted in position, suitable irradiation may be performed in accordance with the diopter of the eye 111. Lenses may be used for the eyepiece portion in this embodiment, but other optical components such as spherical mirrors may also be used.

Light which is produced by reflection, fluorescence, or scattering on a fundus of the eye 111 then travels in the reverse direction along the same path as in the case of incident light. A part of the reflected light is reflected by the light division portion 106 to the wavefront sensor 115 to be used for measuring a light beam wavefront.

In an exemplary embodiment, a Shack-Hartmann sensor is used as the wavefront sensor 115. However, an exemplary embodiment is not limited to a Shack-Hartmann sensor. Another wavefront measurement unit, for example, a curvature sensor may be employed or a method of obtaining the wavefront by reverse calculation from the spot images may also be employed.

In FIG. 1A, when the reflected light passes through the light division portion 106, a part thereof is reflected on the light division portion 104 and is guided to a light intensity sensor 114 through a collimator 112 and an optical fiber 113. The light intensity sensor 114 converts the light into an electrical signal. The electrical signal is processed by a control unit 117 into an image of the subject, and the image is displayed on a display 118.

The wavefront sensor 115 is connected to an adaptive optics control unit 116. The received wavefront is transferred to the adaptive optics control unit 116. The wavefront adjustment device 108 is also connected to the adaptive optics control unit 116 and performs modulation as instructed by the adaptive optics control unit 116. The adaptive optics control unit 116 calculates a modulation amount (correction amount) to obtain a wavefront having no aberration based on the wavefront obtained by measuring a result of the wavefront sensor 115, and instructs the wavefront adjustment device 108 to perform the modulation according to the modulation amount. The wavefront measurement and the instruction to the wavefront adjustment device are repeated and feedback control is performed so as to obtain a suitable wavefront.

In an exemplary embodiment the light division portions 104 and/or 106 are fused fiber couplers. In an alternative exemplary embodiment, the light division portions 104 and/or 106 may include partially reflective mirrors. In another alternative exemplary embodiment, the light division portions 104 and/or 106 may include dichroic reflectors, in which case a different wavelength of light is used for obtaining an image of the fundus then is used for detecting the spatial phase image that controls the adaptive optics system.

The detector 114 may detect reflections or fluorescence associated with the scanning spot. The detection system may make use confocal microscopy techniques in which an aperture associated with the scanning spot is used to increase the resolution and/or contrast of the detection system.

The adaptive optics system described above includes at least the wavefront sensor 115 and the wavefront adjustment device 108 so that the aberration of the subject's eyes can be measured and compensated for. A deformable mirror (DM) or a spatial light phase modulator (SLM) can be used as the wavefront adjustment device 108. Since the typical SLM has a large number of actuators, it can modulate wavefront more precisely than DM can. A liquid crystal on silicon spatial light modulator (LCOS-SLM) may be used as the wavefront adjustment device 108. The LCOS-SLM 108 can be controlled to provide a precise spatial modulation of the phase of the beam that is used to illuminate the subject.

Opthalmoscope 2

Figure 1B:
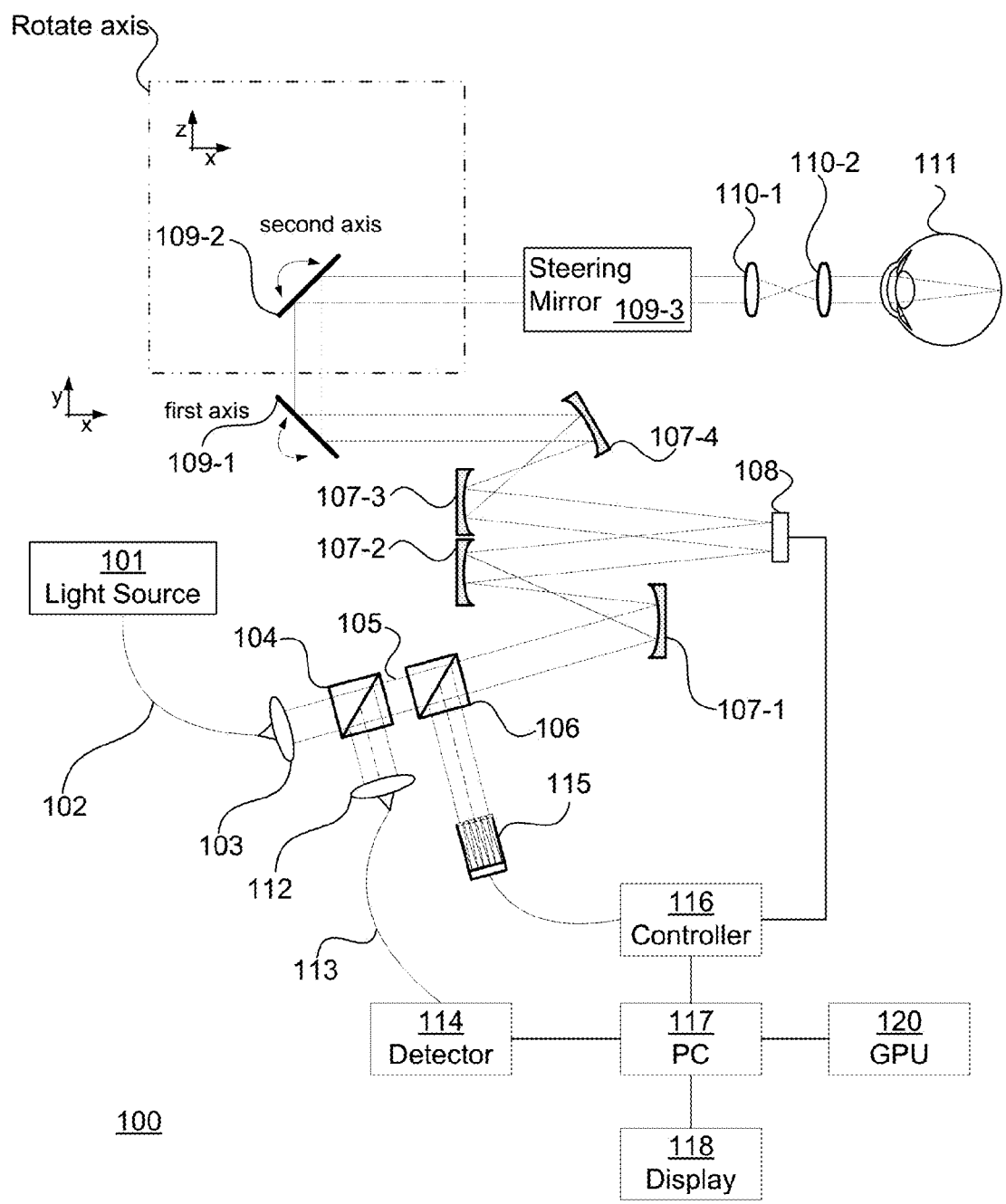

FIG. 1B is an illustration of an alternative embodiment that includes steering mirror 109-3. The steering mirror 109-3 may be a tip-tilt mirror or a pair of scanning mirrors. The steering mirror 109-3 may include galvano, piezo, or mems based mirrors. The steering mirror 109-3 is an optical device that steers the position of the optical beam and may be based upon one or more devices that do not use mirrors such as a spatial phase modulation based steering techniques, lens based steering techniques, electro-optical steering, electro-magnetic steering, or magneto-optical steering.

Multiple Images

The opthalmoscope 100 may take several images and average them together to improve the signal/noise ratio and/or contrast ratio of a final image. The opthalmoscope 100 may take several images and stitch them together to improve the field of view while maintaining the spatial resolution. The opthalmoscope 100 may take several images over period of time to create a fundus time study. These multi-image studies can be difficult to produce efficiently because the eye moves continuously during imaging. When the field of view is small such as in AO-SLO the eye movement can be quite large compared with the image size and the imaging area can sometimes go out of frame due to the eye movement. This can increase the amount of time needed to take an image, especially if multiple images are required.

Eye Tracking

An eye position tracking system may detect the eye's position with a position detection device and shift the imaging area according to the eye movement using tracking mirrors.

The tracking mirrors may be implemented using the scanning mirrors 109-1 and 109-2. In an alternative embodiment, an additional scanning mirror or scanning mirrors may be used to compensate for the detected changes in eye position.

In an embodiment, the position detection system may be both fast and robust. The position detection system may be an image-based eye tracking process for an AO-SLO such as opthalmoscope 100. The process may be implemented in a real-time AO-SLO system and may work well with high-contrast images such as cone mosaic structure of the retina.

Figure 2A:
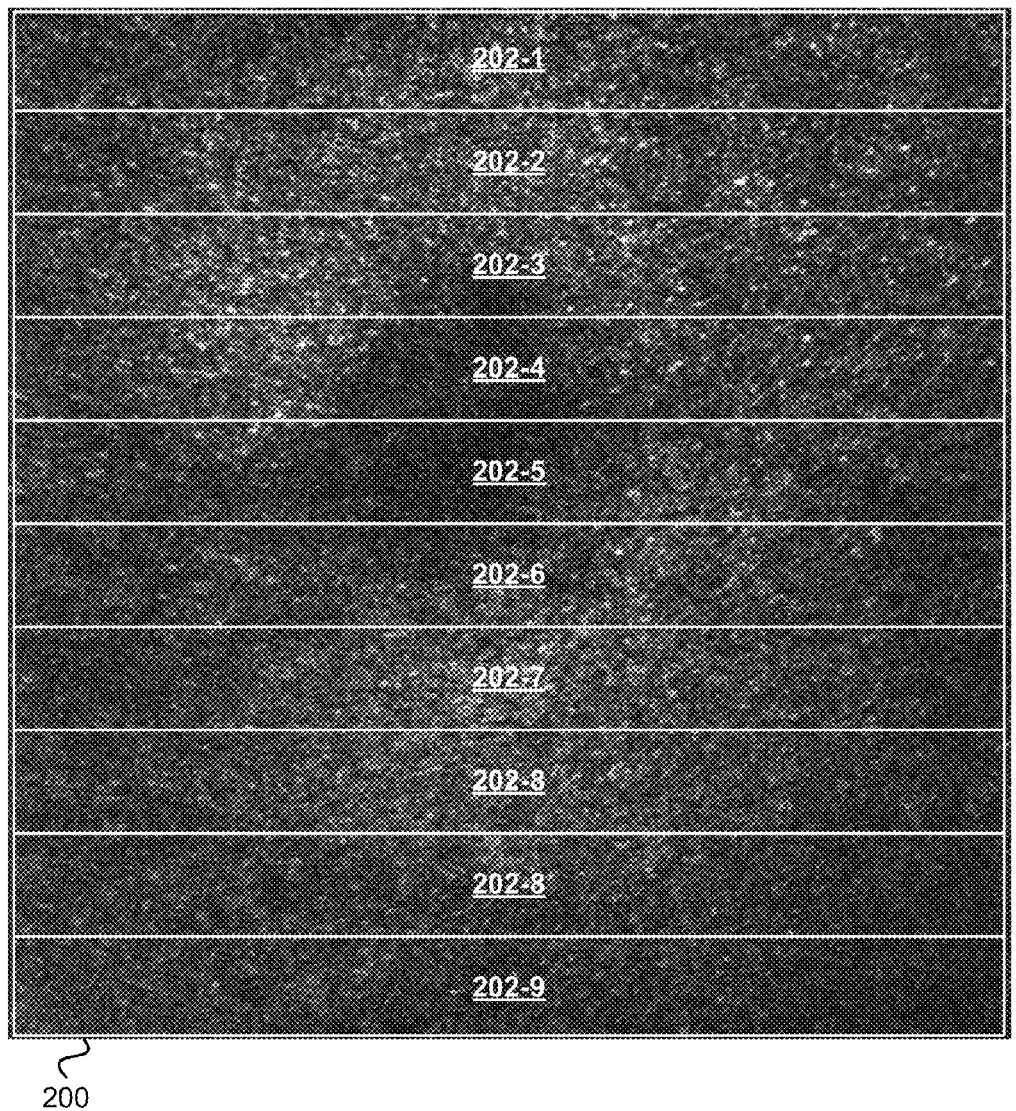
FIGS. 2A-F is an illustration of images that are divided into strips that may be produced in an embodiment.

In order to compensate for intra-image distortion, a full frame of target image 200 is divided into multiple strips 202 (202-1-202-9), as illustrated in FIG. 2A. Whenever a strip 202-1, (e.g., 16 lines) of image 200, is digitized, it may be sent to a PC 117 or some other apparatus that is used for image processing. The PC 117 may include one or more GPU(s) 120. The one or more GPUs 120 may implement processes for calculating motion based on the strips 202.

Figure 3A:
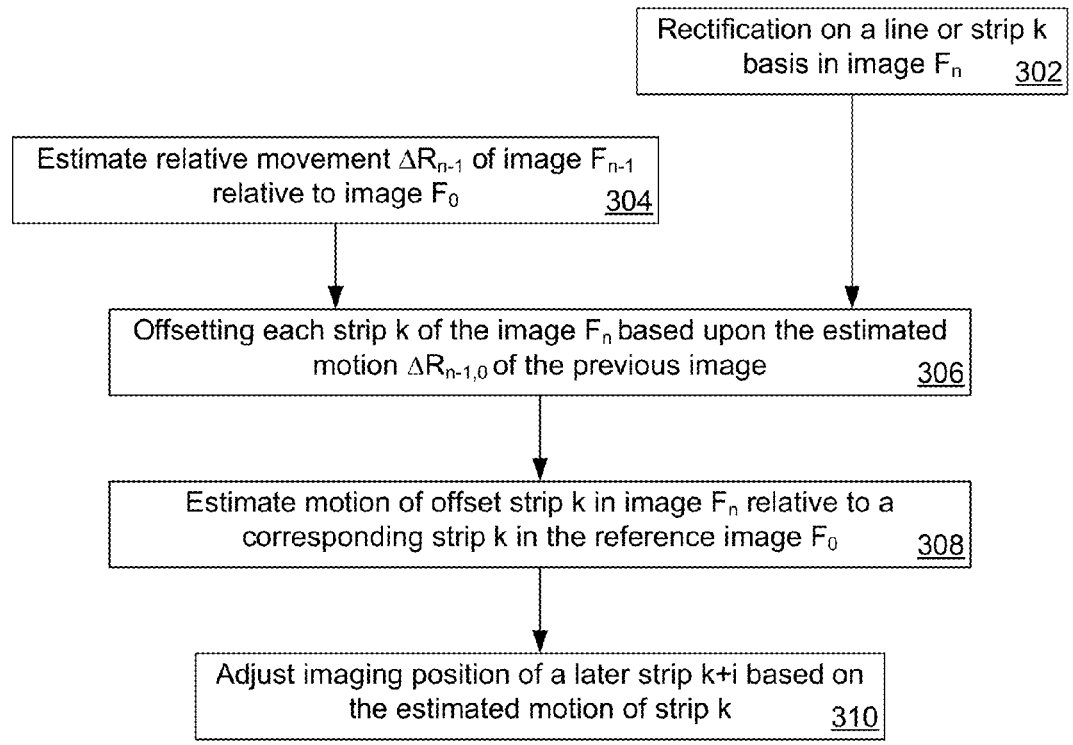
FIGS. 3A-B are illustrations of methods that may be implemented in an embodiment.

After having received an image strip 202, the one or more GPUs 120 perform multiple steps in a process 300 illustrated in FIG. 3A. The multiple steps may be done sequentially. Some of the steps may be done in parallel. A first step 302 of the process 300 may be an optional rectification step 302 that corrects sinusoidal distortion caused by the resonant scanner 109-1. The first step 302 may be skipped if a resonant scanner is not used. The rectification step 302 may be done on a line by line basis or on a strip by strip basis.

Figure 2B:
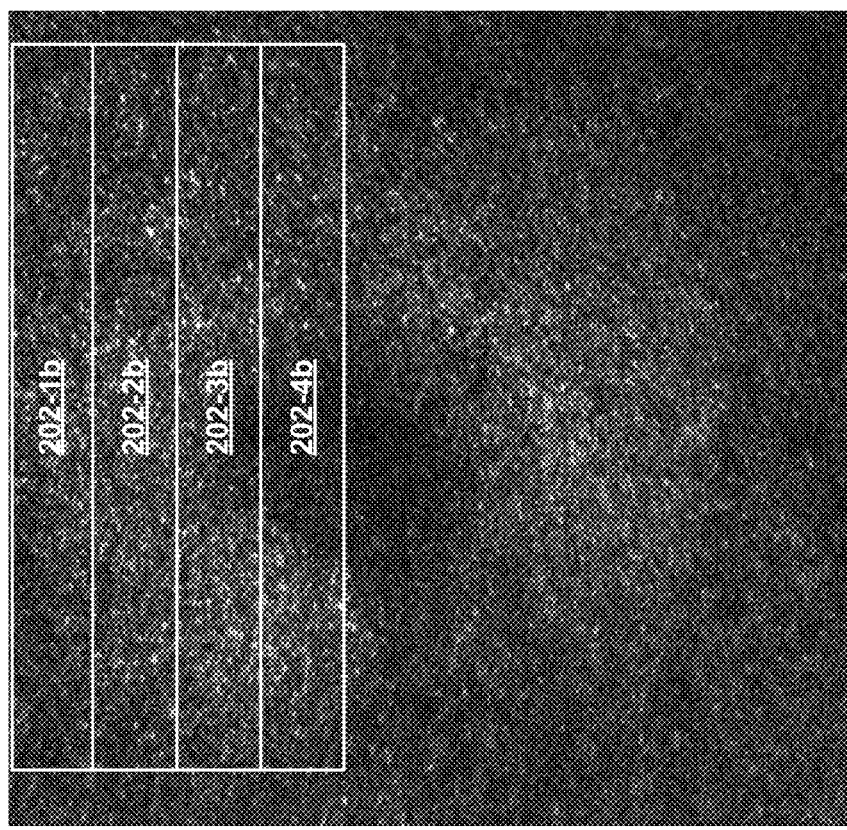
Figure 2B:
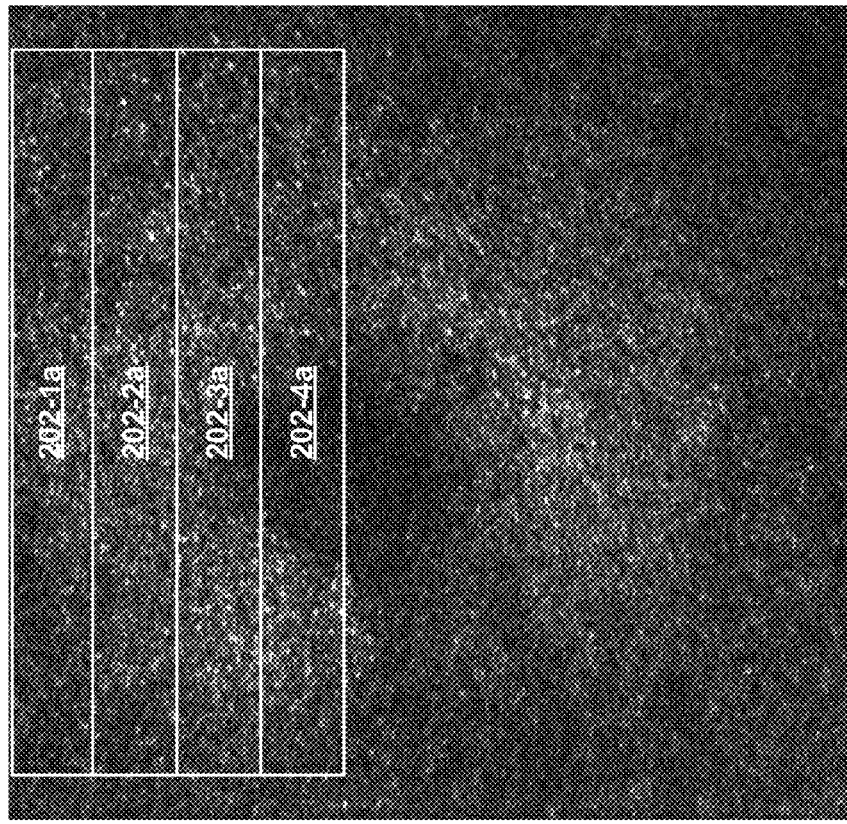

The process 300 may detect large eye motion. These larger motions may be caused by microsaccades. An estimation of the large eye motion may be calculated using image motion analysis between strips 202-#b from the current image $F_n$ 200 -b and a corresponding strip 202-#a from the previous image $F_{n-1}$ 200 -a, as illustrated in FIG. 2B. For example a cross-correlation of strip 202-1b to strip 202-1a may be used to estimate the motion. FIG. 2B is an illustration of an image $F_n$ (200-b) with four strips (202-1b, 202-2b, 202-3b, 202-4b). The detection of microsaccades may be conducted in only the first few strips, e.g., 4, instead of the whole image depending on the computation resources available when the microsaccades detection is performed. The scanning of the rest of the image 200-b may skipped if the motion detected is greater than a first motion threshold. The first motion threshold may be based on the ability of the tracking system to compensate for the motion in time for the rest of the image to be obtained. In an embodiment, the process 300 may include attempting to obtain a new image immediately after the scanning the rest of the image is stopped or delaying obtaining the new image.

Figure 2C:
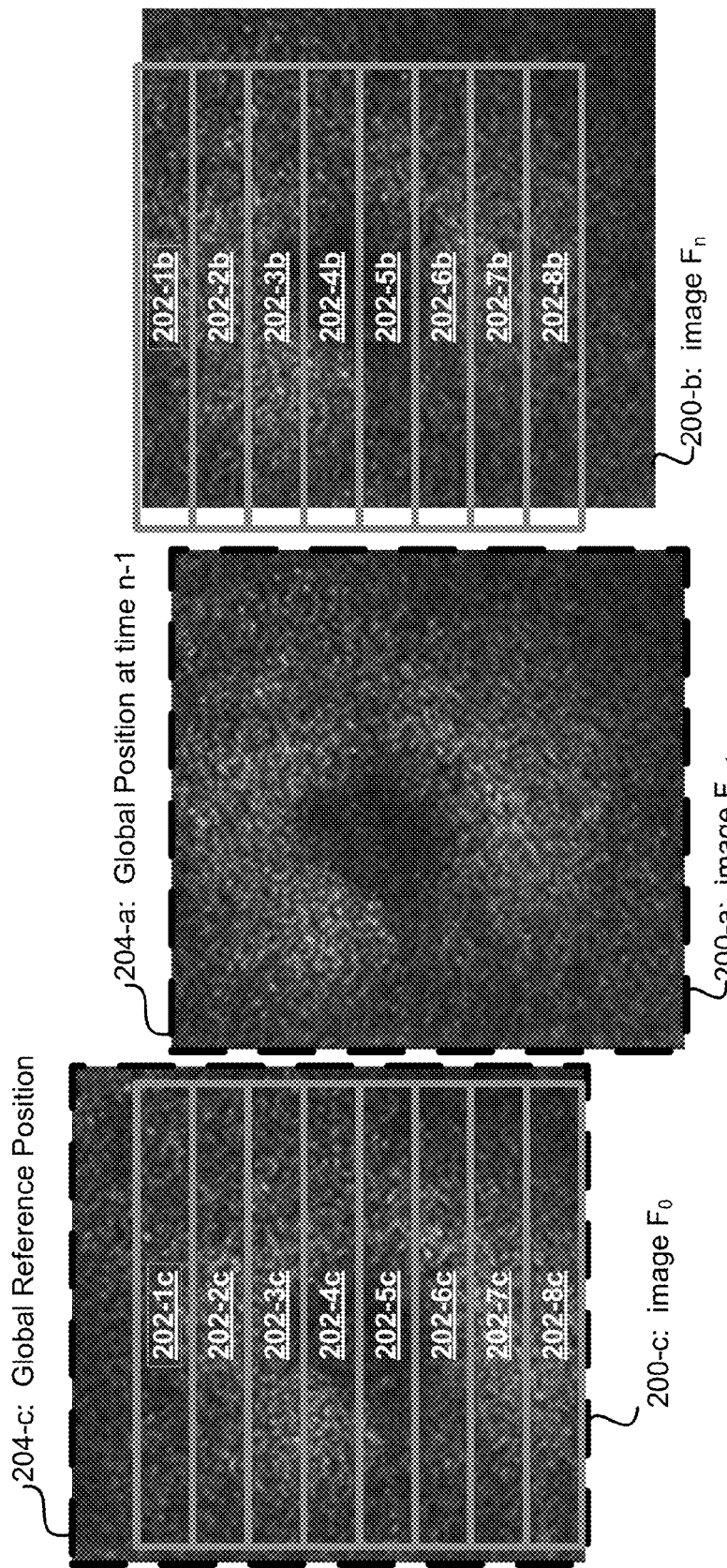

The process 300 may make use of a (global) reference image $F_0$ (200-c) as illustrated in FIG. 2C. Wherein the subscript "0" identifies those images and strips associated with a global reference image. The dashed line 204-c is representative of an area of the reference image associated with the global reference position $\vec{R}_0$ as illustrated in FIG. 2D.

Figure 2D:
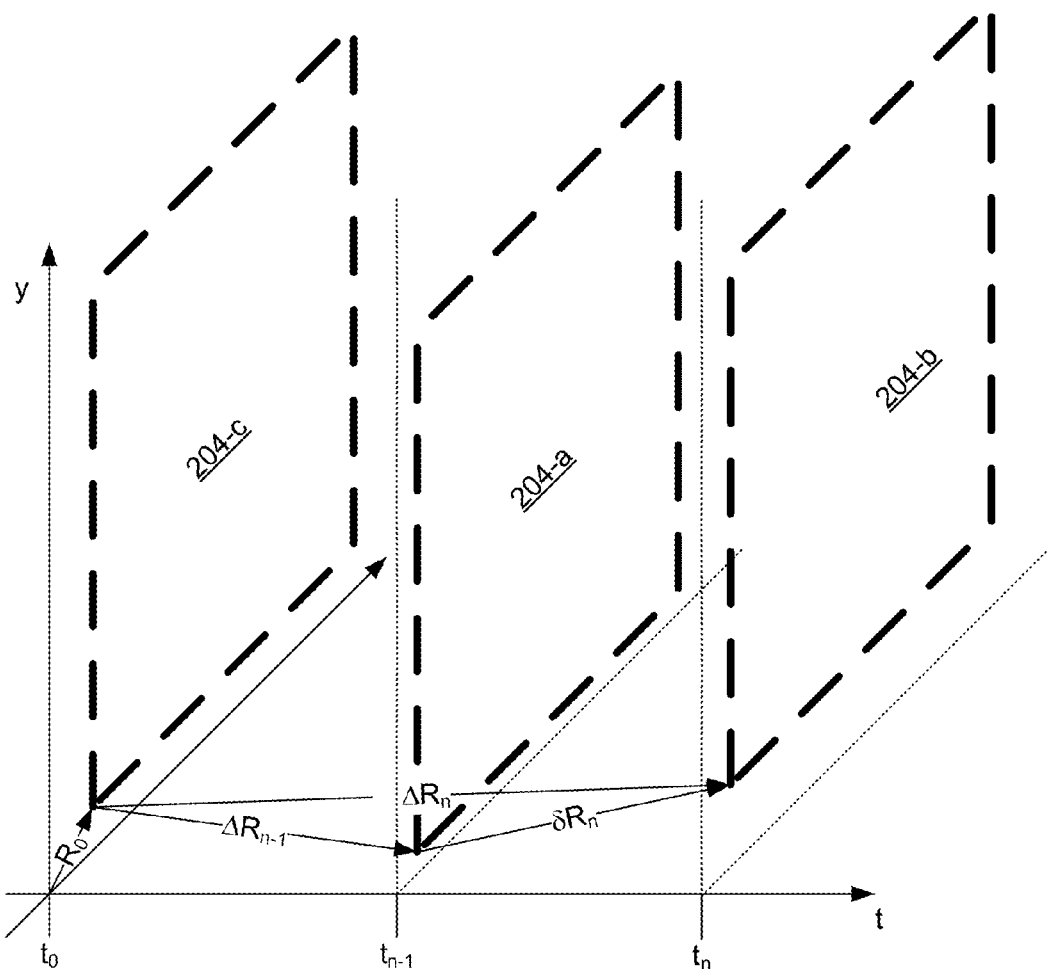

FIG. 2D is illustration of the estimated motion of the areas of the images. The x-y plane is represented as intersecting with the plane of FIG. 2D in an oblique projection, while time is represented along the horizontal axis. Dotted lines parallel to the x axis and the y axis illustrate the relative positions of the axes at a time n−1 and a time n.

The process 300 may estimate the eye motion based on a comparison of the strip $S_{n,k}$ 202 -#b from the current image $F_n$ (200-b) and a corresponding strip $S_{n,k}$ 202 -#c from the (global) reference image $F_0$ (200-c). The subscript "n" is an integer that is used to uniquely identify those images and strips that are currently being obtained at a time n. Wherein k is an integer used to uniquely identify each strip in the image. The previously calculated image motion of an image $F_{n-1}$ (200-b) may be used to offset the position of the current strips (202-#b), as illustrated in FIG. 2C. The subscript "n−1" is in reference to the most recent previous images and strips. The dashed line 204-a is representative of the position $\vec{\Delta R}_{n-1}$, of the most recent image relative the global reference position $\vec{R}_0$ as illustrated in FIG. 2D. The estimated motion from each strip may be sent to a fast tip/tilt mirror (TTM) to dynamically track location of the eye 111 such as steering mirror 109-3.

The motion of the most recent image $\vec{\Delta R}_{n-1}$, may be represented by two estimated values along two orthogonal axes ($\Delta X_{n-1}$, $\Delta Y_{n-1}$). In an alternative embodiment, the estimated values for $\vec{\Delta R}_{n-1}$ may also include additional variables such as torsion or depth. The two estimated values ($\Delta X_{n-1}$, $\Delta Y_{n-1}$) may be used for offsetting all of the detected strips 202-#b relative to the reference image $F_0$ (200-c). The offset strips which are then used to calculate the strip motion between the reference image $F_0$ (200-c) and the current image $F_n$ (200-b). This offset can reduce computational costs. The offset may then be added back to each strip to obtain its true motion relative to the reference image $F_0$ (200-c).

When the entire image 200-b has been obtained, after motion from all of the strips 200-#b have been estimated, a process that may be implemented on the GPU that calculates the relative image motion $\vec{\Delta R}_n$ of the entire image $F_n$ (200-c) relative to the reference image $F_0$, which is used to offset positions of strips for the next image $F_{n+1}$. The image motion $\vec{\Delta R}_{n-1}$ may be calculated on the basis of the entire image or it may be calculated on a strip by strip basis.

As described above the process 300 may include the optional step 302 of rectification. The rectification step 302 may be done as each line is obtained or on multiple lines at once if it is done a strip by strip basis. Wherein, the rectification step 302 is performed on a strip k of the image $F_n$.

The process 300 may also include a step 304 in which the movement of the previous image $F_{n-1}$ relative to a reference image $F_0$ is calculated as $\vec{\Delta R}_{n-1}$. In one embodiment, the movement $\vec{\Delta R}_{n-1}$ is calculated by comparing the entire previous image $F_{n-1}$ relative to the entire reference image $F_0$. In another embodiment, the movement $\vec{\Delta R}_{n-1}$ may be calculated by comparing one or more of each strip k in image $F_{n-1}$ to a corresponding strip k in reference image $F_0$ on a strip by strip basis or by comparing each strip k to the entire reference image $F_0$ to identify large motions. The movement of one or more of the strips k may be estimated and one or more of these estimates may be used to estimate a $\vec{\Delta R}_{n-1}$ final movement of the previous image $F_{n-1}$ relative to the reference image $F_0$. The movement may be estimated using cross-correlation imaging tracking techniques or other methods.

The cross correlation technique may involve calculating the convolution or correlation of the first image and an offset of the second image as illustrated in equation (1).

$$A_{n-1}(\vec{B}_{n-1}) = \qquad (1)$$
$$(F_0 \star F_{n-1})[\vec{B}_{n-1}] = (F_0 * F_{n-1})[\vec{B}_{n-1}] = \sum F_0 F_{n-1}(\vec{B}_{n-1})$$
$$[A_{n-1,max}, \vec{B}_{n-1,max}] = \max_{\vec{B}_{n-1}}(A_{n-1}(\vec{B}_{n-1}))$$
$$\vec{\Delta R}_{n-1} = \vec{B}_{n-1,max}$$

For real images, the convolution function is equivalent to the correlation function. For discrete images, a summation function is used instead of an integration function. The summation is performed over the area of the images $F_0$ and $F_{n-1}$. The vector $\vec{B}_{n-1}$ is an arbitrary vector for representing the trial offsets of image data $F_{n-1}$ relative to $F_0$. The function A is representative of the results of the correlation function. The function A is evaluated for several trial vectors $\vec{B}_{n-1}$ and the maximum value for the function A is sought out. $\vec{\Delta R}_{n-1}$ is that vector $\vec{B}_{n-1}$ at the maximum value of the function A. A peak search method may also be used to refine the value $\vec{\Delta R}_{n-1}$. Other methods may be used to find $\vec{\Delta R}_{n-1}$ using some quantitative method of comparing the reference image $F_0$ and the offset image $F_{n-1}$.

The process 300 includes a step 306 of offsetting each strip k of the image $F_n$ based upon the estimated motion $\vec{\Delta R}_{n-1}$ of the previous image as illustrated in FIG. 2C. The process may also include an estimation step 308 in which each offset strip k is compared to a corresponding strip k in reference image $F_0$ to obtain an estimation of movement $\vec{\Delta R}_{n,k}$ of the strip k in image $F_n$ relative to the reference image $F_0$ which is correlated with the movement of the subject 111 relative to the reference position. The estimation step 308 may be performed by using cross-correlation and/or other image based motion estimation/tracking methods. The process 300 may include a compensation step 310 in which estimated movement $\vec{\Delta R}_{n,k}$ of the strip k in image $F_n$ relative to the reference image $F_0$ is then used to reposition the scanning area in the subsequent strip k+1 or a later strip k+x in which x is greater than 1 and depends on the processing time. The offset $\vec{\Delta R}_{n-1}$ may be removed to give a measure of the current motion relative to the most recent image. The compensation step 310 may include adjusting the scanners 109-1 and 109-2. The compensation step 310 may instead make use of an additional tip/tilt scanner 109-3 or set of scanners that are used specifically for positioning the scanning area instead of the scanners which are used for scanning the measurement beam.

Robust Tracking Method

As discussed above we may define strip motion between the reference image $F_0$ and the target image $F_n$ with a vector $\vec{\Delta R}_{n,k}$ ($\Delta X_{n,k}$, $\Delta Y_{n,k}$) where n is an image index of the target image $F_n$ and k is strip index from the target strip $S_{n,k}$, and define strip motion between the two corresponding strips ($S_{n,k}$, $S_{n-1,k}$), in two consecutive images, target image $F_n$ and its previous image $F_{n-1}$, as $\vec{\delta R}_{n,k}$ ($\delta X_{n,k}$, $\delta Y_{n,k}$). The applicants have found that it is useful to verify the self-consistency of the estimated motion with the following approximation equation (2a). Where $\vec{\Delta R}_{n-1,k}$ ($\Delta X_{n-1,k}$, $\Delta Y_{n-1,k}$) is strip motion between image $F_{n-1}$ and the reference image $F_0$. Equation (2b) is reformulation of equation (2a) to come up with a quality metric $Q_{n,k}$ as a comparison test. In equation (2b) illustrates how the vector $\vec{\Delta R}_{n-1,k}$ is added to the vector $\vec{\delta R}_{n,k}$ the vector $\vec{\Delta R}_{n,k}$ is then subtracted from this vector sum. The applicants have found that magnitude $Q_{n,k}$ of this calculation can be used as estimation of the quality of the tracking estimation. The quality metric $Q_{n,k}$ may then be compared to a threshold $R_{max}$. If the quality metric $Q_{n,k}$ is less than a threshold $R_{max}$ as described equation (2c) then eye tracking estimation may be considered good enough for controlling the motion of a tracking mirror.

$$\vec{\Delta R}_{n,k} \approx \vec{\Delta R}_{n-1,k} + \vec{\delta R}_{n,k} \quad (2a)$$

$$Q_{n,k} = |\vec{\Delta R}_{n-1,k} + \vec{\delta R}_{n,k} - \vec{\Delta R}_{n,k}| \quad (2b)$$

$$R_{max} > Q_{n,k} \quad (2c)$$

The quality metric $Q_{n,k}$ is representative of the quality of: eye tracking estimation of the current image, eye tracking estimation of the previous image, the current image; and the previous image.

Figure 2E:
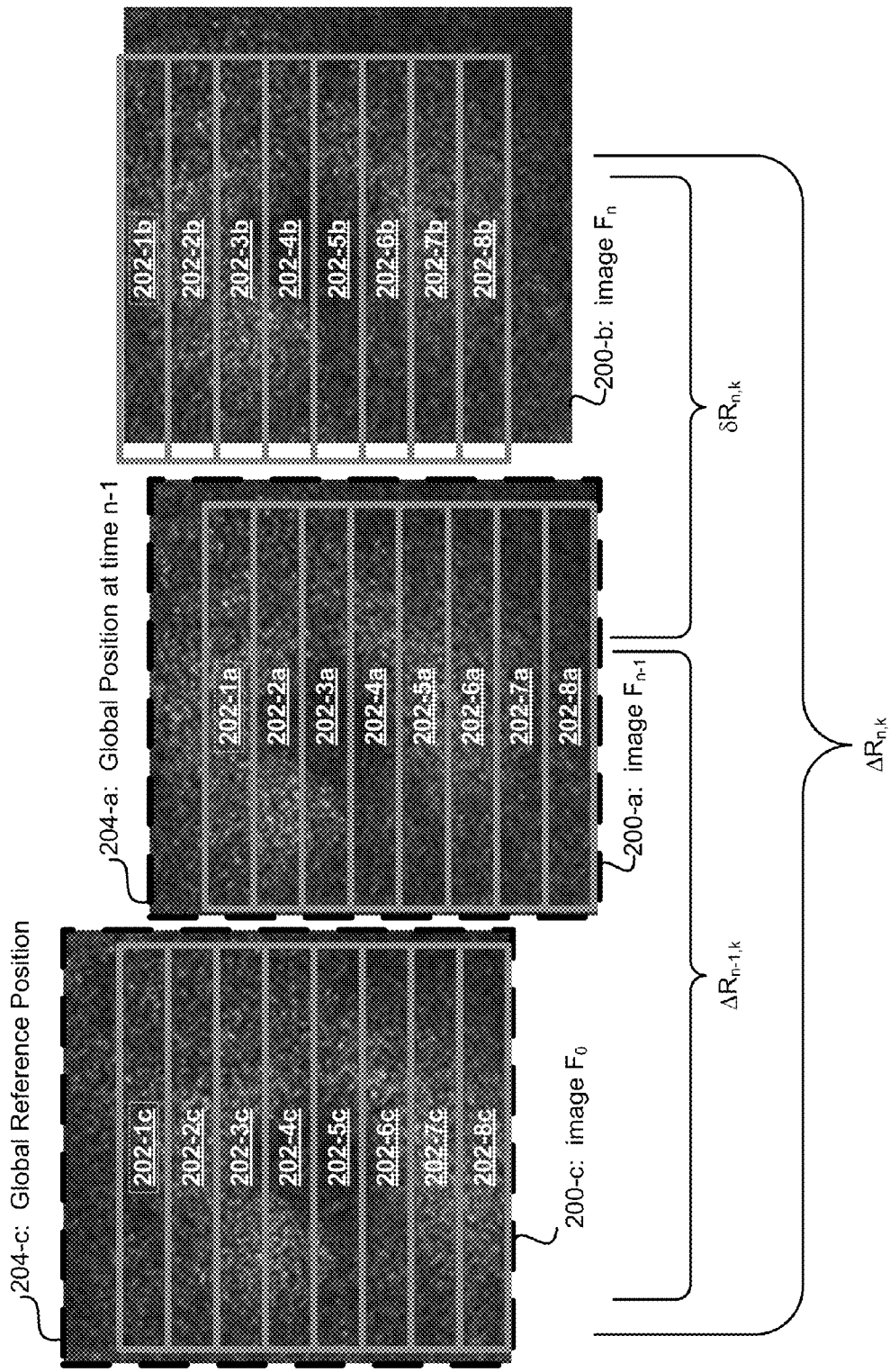

FIG. 2E is an illustration of the how the different images may be used to estimate the target strip motion $\vec{\Delta R}_{n,k}$ with data from strips between two consecutive images $\vec{\delta R}_{n,k}$.

Due to the fluctuation of image brightness and contrast, noise level, and possible eye torsion, calculation of the target strip motion $\vec{\Delta R}_{n,k}$ between the target image $F_n$ and the reference image $F_0$ as time intervals increase to seconds or tens of seconds, becomes less reliable. The calculation can become less reliable as the cross correlation method can provide a false positive by finding a false peak location. However, the estimation of $\vec{\delta R}_{n,k}$ from two consecutive images ($F_n$, $F_{n-1}$) is substantially more reliable because the time interval can be on the order of tens of milliseconds, instead of seconds. Thus fluctuations in image brightness, contrast, noise level, and eye torsion have significantly less negative impact on the calculation of $\vec{\delta R}_{n,k}$. Therefore, $\vec{\delta R}_{n,k}$ may be used to further estimate $\vec{\Delta R}_{n,k}$ where $\vec{\Delta R}_{n,k}$ may be replaced by $\vec{\Delta R}_{n-1,k} + \vec{\delta R}_{n,k}$ if the cross correlation returns an unreasonable $\vec{\Delta R}_{n,k}$.

Figure 3B:
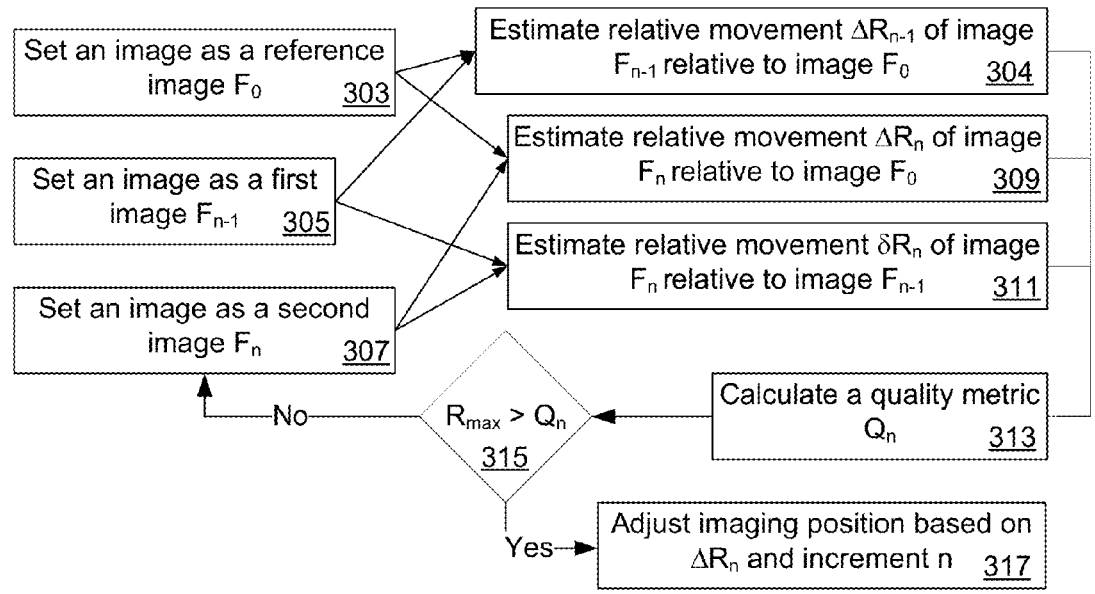

FIG. 3B is an illustration of a method 301 which may implement the robust tracking method which may be used in an embodiment. The method 301 may include a step 303 of setting an image as a reference image $F_0$. The method 301 may include a step 305 of setting an image from among a plurality of images as a first image $F_{n-1}$. The method 301 may include a step 307 of setting an image from among a plurality of images as the second image $F_{n-1}$. The second image may be an image obtained immediately after the first image is obtained. The second image may be an image of the same area as the first image obtained most recently after the first image was obtained that also meets certain criteria, such as lack of interference from an eye lash or a blink.

The method 301 may include the step 304 as used in method 300 in which the movement of the first image $F_{n-1}$ relative to a reference image $F_0$ is estimated as $\vec{\Delta R}_{n-1}$. The method 301 may include a step 309 in which the movement of the second image $F_n$ relative to a reference image $F_0$ is estimated as $\vec{\Delta R}_n$. The method 301 may include a step 311 in which the movement of the second image $F_n$ relative to the first image $F_{n-1}$ is estimated as $\vec{\delta R}_n$.

The method 301 may include a step 313 of calculating a quality metric $Q_n$ such as using equation (2c) based on $\vec{\Delta R}_{n-1}$, $\vec{\Delta R}_n$, and $\vec{\delta R}_n$. The method 301 may include a step 315 of comparing the quality metric $Q_n$ to a threshold $R_{max}$. In a first case wherein the quality metric meets threshold criteria the method may include a step 317 in which the imaging position is adjusted based on the estimated relative change in position $\vec{\Delta R}_n$. The step 317 may also include incrementing index n, in which case the second image becomes the first image, a new second image, and estimation and calculation steps are calculated for the new index n. In a second case in which the quality metric does not meet the threshold then a new second image is obtained in step 307. In which case new estimates and metrics are calculated and compared. The method 301 may be done repeatedly forming a feedback loop and may be done for full images or for sub-images such as strips.

Pre-Processing of Images

When obtaining low-contrast images, including vascular images, additional pre-processing of raw images may be employed before cross-correlation is performed. The pre-processing may start with a 2-dimensional smoothing filter, followed by a 2-dimensional Sobel filter, and followed by thresholding to remove filtering artifacts. Filter combinations may be switched according to image signal strength, FOV size and focusing position.

Figure 4:
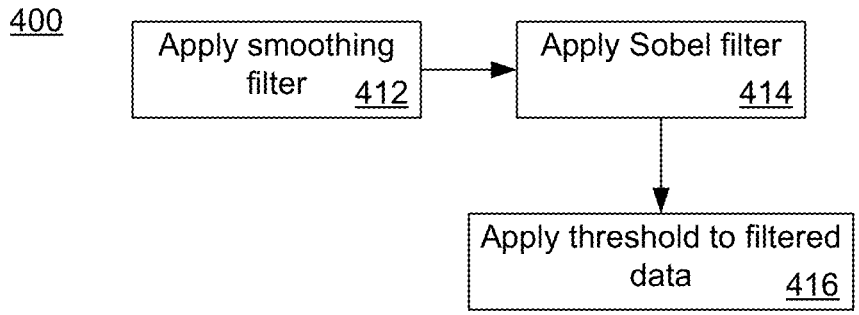
FIG. 4 is an illustration of a method that may be implemented in an embodiment.

FIG. 4 is an illustration of a pre-processing method 400 described above. The pre-processing step may be performed before or after the optional rectification step 302. The pre-processing method 400 may be performed on a strip by strip basis or on a line by line basis to the image data obtained by the detector 114. The pre-processing method 400 may be performed by one or more of a PC 117, a GPU 120, and/or dedicated circuitry.

The pre-processing method 400 may include an optional first pre-processing step 412 of applying a smoothing filter to the image data obtained by the detector 114 to obtain smoothed image data. The smoothing filter in the first pre-processing step 412 may be a two-dimensional smoothing filter. Applying the smoothing filter may include convolving a filter function with the image data. The smoothing filter may be a single pass or a multi-pass filter. One or more different kinds of filter functions may be used including Gaussian filters, hat filters, adaptive filters, and other filter functions. Other methods of applying a smoothing filter may also be used all of which include methods of reducing noise in the input image data with the end results of producing smoothed image data with less noise.

The pre-processing method 400 may include an optional second pre-processing step 414 of applying a Sobel filter to the smoothed image data or the image data from the detector 114. Applying the Sobel filter may include convolving data with a kernel, the kernel may be a Sobel kernel or other similar kernels.

The pre-processing method 400 may include an optional third pre-processing step 416 of applying a thresholding step. The thresholding step 416 may include applying a specific threshold or an adaptive threshold to data produced in the previous pre-processing steps. The threshold step 416 may be used remove artifacts produced by the previous filtering steps.

Adaptive Strip Size

Figure 5:
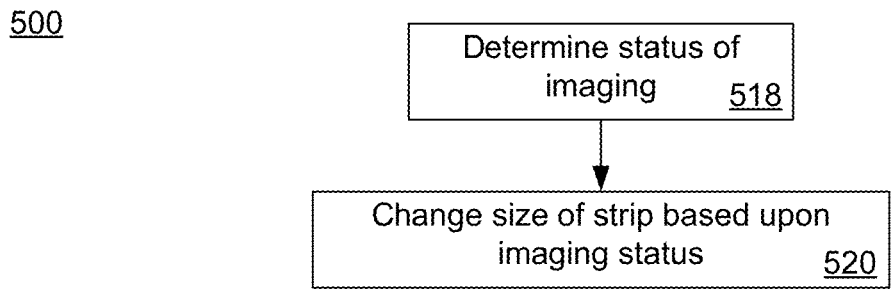
FIG. 5 is an illustration of a method that may be implemented in an embodiment.

In order to improve upon the quality of low-contrast images, including vascular images, a size of strips may be changed as illustrated in an adaptive strip size method 500 illustrated in FIG. 5. The inventors have found that with larger strips the accuracy and robustness of cross-correlation is higher. Although, when the strip size is increased then the time that the imaging system needs to respond to the subjects, motion is decreased. In one alternative embodiment, the number of lines of image data used in a strip to perform cross-correlation so as to estimate the position of the subjected being is changed (increased or decreased) while the image is being obtained.

A first step 518 in the adaptive strip size method 500 may be determining the status of the current image as it is being obtained. The status of the image may include one or more of: magnification; resolution; spot size; focal point; relative imaging position on the subject's fundus; light intensity; wavelength; statistics associated with image properties such as image signal strength and contrast ratio; higher order image data statistics such as the distribution and number of distinct features that can be identified in the imaging area of the strip; measures of the reliability of the cross-correlation estimation as used in the particular strip or a recent strip; peak value of the cross-correlation function in the current particular strip or a previous particular strip; the width of the peak; and/or the amount of position shift detected. One or more of these values may then be compared to one or more thresholds. The results of these comparisons can give an estimation of the robustness of the current strip and its ability to give a quality estimate of the motion of the subject.

A second step 520 in the adaptive strip size method 500 may be changing the size of the strip based upon the status of the present imaging method. The number of lines used in the current strip may be increased, decreased, or kept the same based upon the determination made in step 518. For instance, if the status of the present imaging method is indicative that the estimation in the change of movement as detected using the current strip size will be less than a particular lower limit threshold then the number lines included in the particular strip may be increased, thus improving the reliability of the position estimation method. Likewise, if the status of the present imaging method is indicative that the estimation in the change of movement as detected using the current strip size will be greater than a particular upper limit threshold then the number lines included in the particular strip can be decreased, thus increasing the speed with which position changes are detected and compensated for.

Microsaccade Detection

In an integrated system where a wide field of view scanning laser ophthalmoscope (WFOV-SLO) and an adaptive optics scanning laser ophthalmoscope (AO-SLO) do eye tracking concurrently, the WFOV-SLO is usually able to detect microsaccades more accurately than the AO-SLO does because of its large scanning FOV. The AO-SLO tracking may be notified dynamically by the WFOV-SLO tracking software when a microsaccade occurs so that AO-SLO tracking software may freeze a tip tilt mirror 109-3 without doing additional computation.

Automatic Reference Image Selection Method

An imaged-based eye tracking process such as the exemplary process 300 illustrated in FIG. 3A makes use of a reference image 204-C $F_0$. The reference image 204-C $F_0$ may be determined manually. In which case an operator chooses a "good" image from a live video stream and an algorithm then drives a scanning system such which may include a tip tilt mirror 109-3 to stabilize all the images following images with respect to the chosen reference image 204-C $F_0$. In real-time human retinal imaging, it can be difficult to predict the occurrence of a blink or a microsaccade. Thus, it is not unusual for an operator to choose a reference image 204-C $F_0$ from a highly distorted microsaccade interval, or from a blink interval in which the reference image 204-C $F_0$ is of poor quality in the context of having suitable features to be used in the cross correlation calculation. When this situation arises, often the best solution is to stop tracking, reset, and use a different reference image 204-C $F_0$. When a patient's eye is unstable, moving too fast, the occurrence of microsaccades or blinks is too frequent, manually choosing a good reference image 204-C $F_0$ can become a problem for an operator. It can be challenging for an operator to manually capture a reference image 204-C $F_0$ from the live video feed.

Figure 2F:
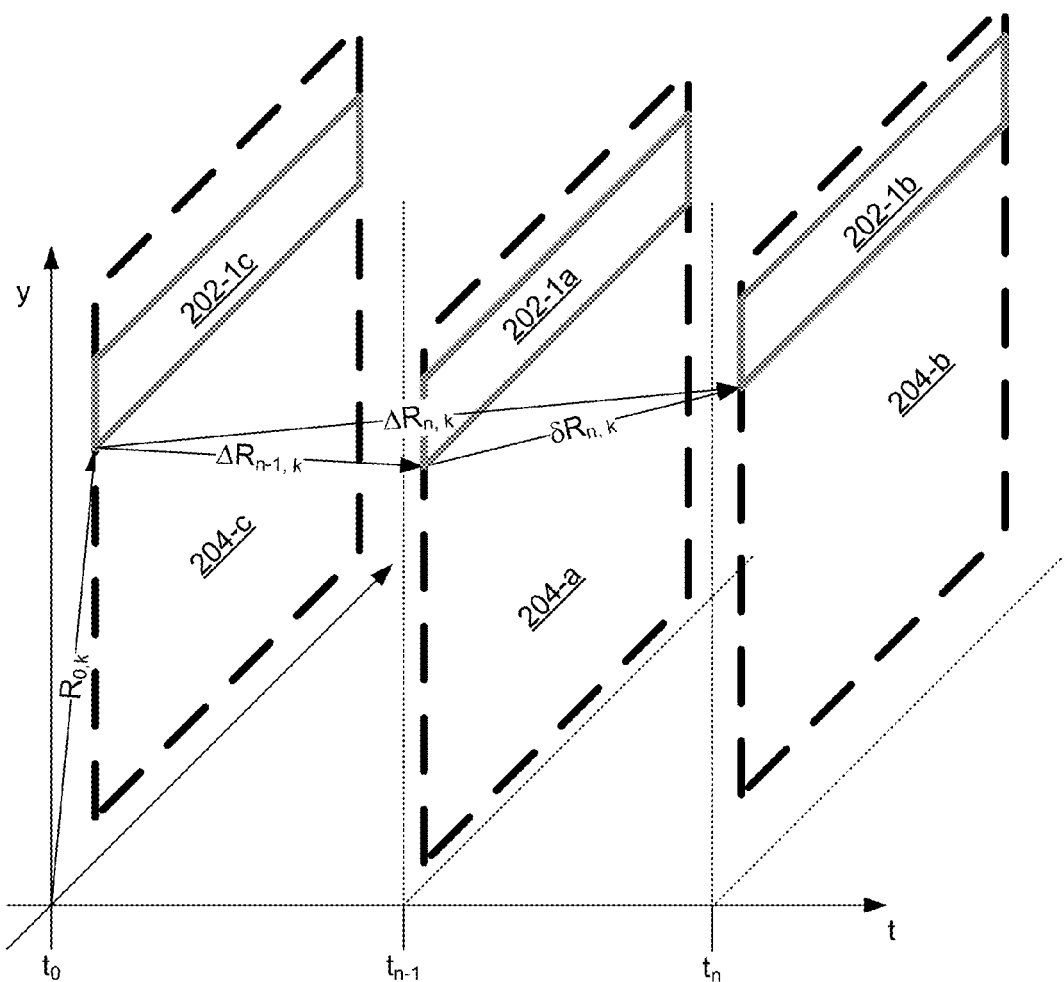
Figure 6:
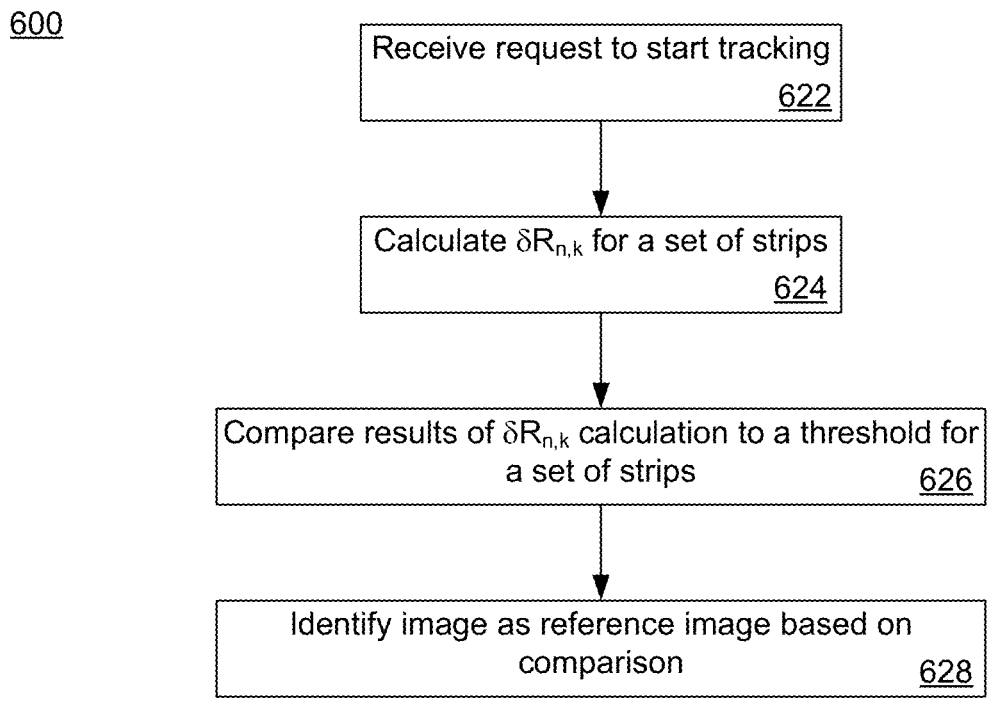
FIG. 6 is an illustration of a method that may be implemented in an embodiment.

A reference image selection method 600 illustrated in FIG. 6 can choose an appropriate reference image for the operator. The reference image selection method 600 may start with when operator pushes a software or hardware button "start tracking". In an embodiment, a processor 764 may receive a request to start tracking in a step 622 of method 600. The criteria for any random reference image for being a 'good' reference image may be based on data obtained from the two consecutive images, i.e., $\vec{\delta R}_{n,k}$ as illustrated in FIG. 2F. In which case, in a calculation step 624 the processor 764 may calculate $\vec{\delta R}_{n,k}$ for one or more strips. $\vec{\delta R}_{n,k}$ may be calculated using the same method described in equation (1) shown here as equation (3). Equation (3) is substantially similar to equation (1). In which each strip $S_{n,k}$ is indexed at a time index n, and a strip index k. The variable $C_{n,k}$ is representative of the results of the cross correlation function for each strip at time index n and strip number k.

$$C_{n,k}(\vec{B}_{n,k}) = \qquad (3)$$
$$(S_{n-1,k} \star S_{n,k})[\vec{B}_{n,k}] = (S_{n-1,k} * S_{n,k})[\vec{B}_{n,k}] = \sum S_{n-1,k} S_{n,k}(\vec{B}_{n,k})$$
$$\left[ C_{n,k,max}, \ \vec{B}_{n,k,max} \right] = \max_{\vec{B}_{n-1}} (C_{n,k}(\vec{B}_{n,k}))$$
$$\vec{\delta R}_{n,k} = \vec{B}_{n,k,max}$$

The reference image selection method 600 may include a comparison step 626. The comparison step 626 may include comparing the results of strip motion calculation to a threshold. In one embodiment, $\vec{\delta R}_{n,k}$ from a set of strips are compared to a threshold. In one embodiment, the set of strips may include all of the strips that make up a particular image. In one alternative embodiment, the set of strips may include all of the strips that make up multiple images. In one embodiment, $C_{n,k,max}$ from a set of strips among one or more images may be compared to a threshold. In another embodiment, statistics associated with the $C_{n,k,max}$ calculation, such as a peak width associated with $C_{n,k,max}$, from a set of strips among one or more images may be compared to a threshold. Multiple different criteria may be compared to multiple different thresholds during the comparison step 626.

The reference image selection method 600 includes an image selection step 628, wherein, the result of the comparison done in step 626 may identify a pair of images $F_n$ and $F_{n-1}$. The identified images are those images that pass the comparison test. Either of these images $F_n$ and $F_{n-1}$ may then be used as a reference image 204-$c$ $F_0$. In a first case, the threshold test identifies an image in which the estimated movement $\vec{\delta R}_{n,k}$ is less than a threshold for all of k in an image n then the images $F_n$ or $F_{n-1}$ may be considered good images and used as the reference image 204-$c$ $F_0$. In a second case, the threshold test identifies an image in which correlation coefficients from a set of strips are higher than a used-defined threshold, then the images $F_n$ or $F_{n-1}$ may be considered good images and used as the reference image 204-$c$ $F_0$.

Method for an Embodiment that Includes a WF-SLO and an AO-SLO

Figure 7A:
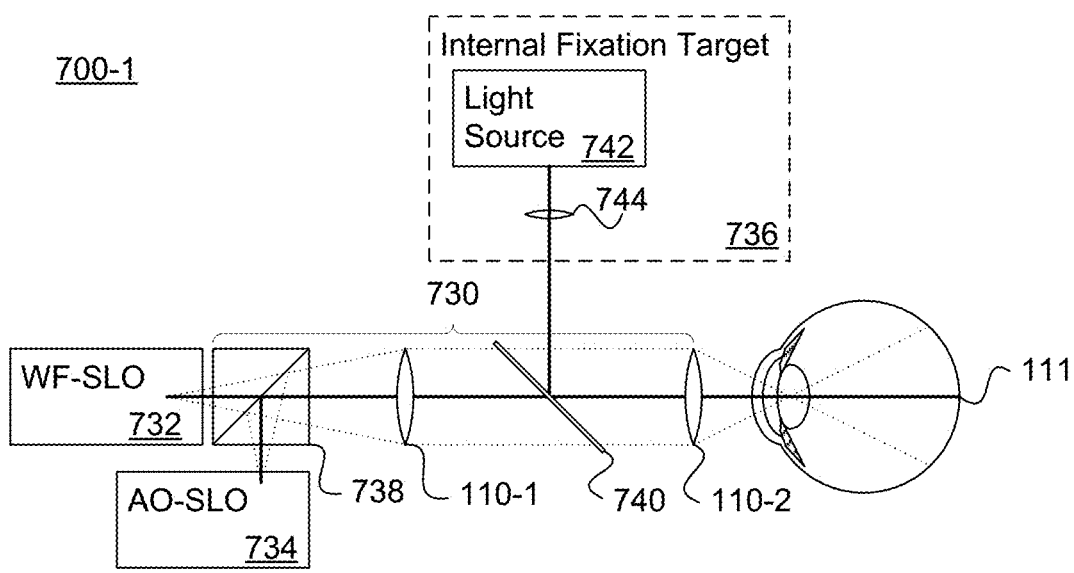
FIGS. 7A-D are illustration of an ophthalmoscopes in which embodiment may be implemented.
Figure 7B:
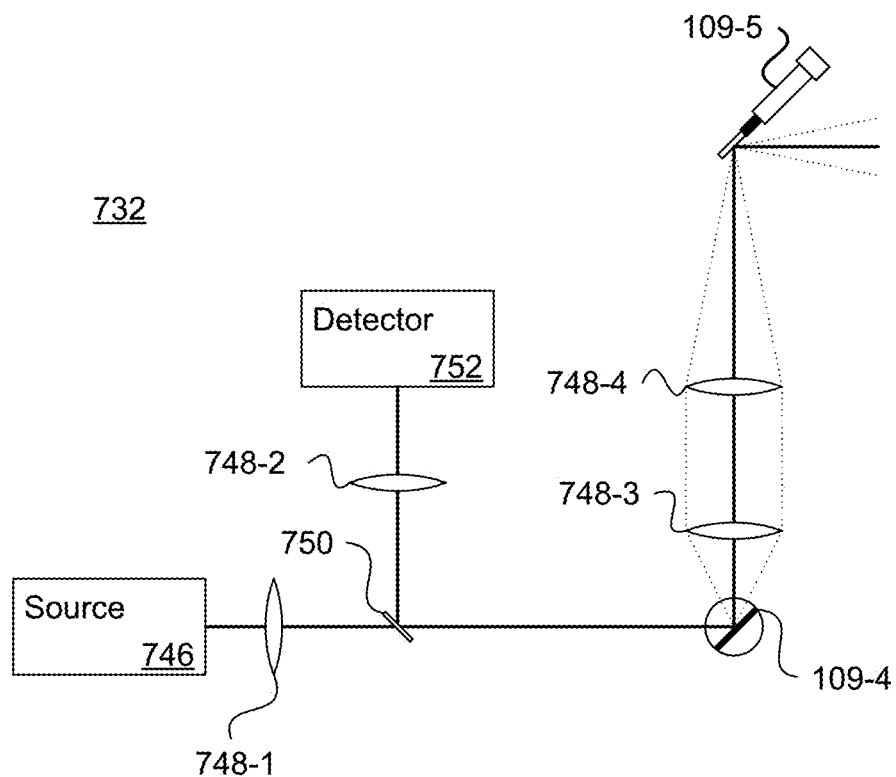
Figure 7C:
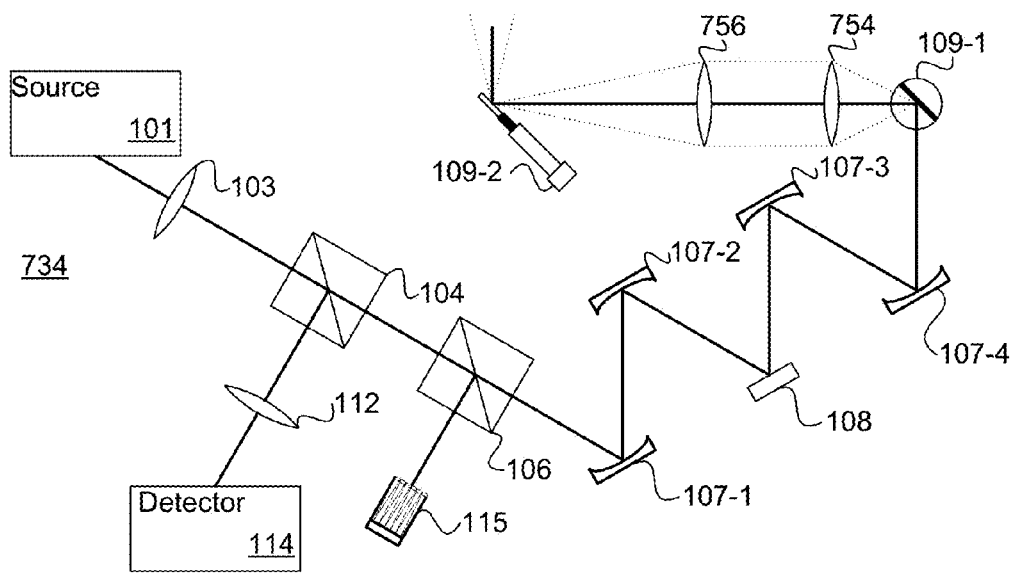

An embodiment may be implemented in an integrated ophthalmoscope 700-1 as illustrated in FIGS. 7A-C. An embodiment may also be a method that is used in the context of the integrated ophthalmoscope 700-1.

The integrated ophthalmoscope 700-1 may be also referred to as the system 700-1 in the context of this application. The ophthalmoscope 700-1 includes an ocular lens unit 730, a wide field scanning laser ophthalmoscope (WF-SLO) 732, an adaptive optics scanning laser ophthalmoscope (AO-SLO) 734, and an internal fixation target 736. A scanning beam of the WF-SLO 732 and a scanning beam of the AO-SLO 734 illuminate a fundus of a subject 111. In one embodiment, the beams enter the fundus simultaneously, and each of the beams may have different wavelengths. In another embodiment, the beams enter the fundus at separate times. This may be done using pulsed light sources, optical switches, a single light source and a dual output Mach-Zehnder modulator, or a variety of other methods in which light can be combined and then independently detected may be used.

The ocular lens unit 730 may include a first beam combiner 738 for combining the beams to and from the WF-SLO 732 and the beams to and from the AO-SLO 734 to form a combined beam. The first beam combiner 738 may include a partially silvered mirror in which case, the beams may have similar wavelengths. The first beam combiner 738 may include a dichroic mirror in which case, wavelength ranges of the beams to and from the WF-SLO 732 may be different from wavelength ranges of the beams to and from the AO-SLO 734. The first beam combiner 738 may be a switch in which case the switch may be used to temporally multiplex beams to and from the WF-SLO 732 and the beams to and from the AO-SLO 734.

The ocular lens unit 730 may also include a first eyepiece or lens 110-1 and a second eyepiece or lens 110-2 which are used to transmit the combined light from the beam combiner 738 to an object 111. The first eyepiece 110-1 and the second eyepiece 110-2 may be replaced with curved mirrors. A dichroic filter 740 may be inserted between the first eyepiece 110-1 and the second eyepiece 110-2 in order to combine the combined light from the beam combiner 738 with light from an internal fixation target 736. In an alternative embodiment, the dichroic filter 740 may be inserted between the second lens 110-2 and the object 111. The internal fixation target 736 may include a first light source 742 and a third lens 744. The first light source 742 may be multiple light emitting diodes arranged in matrix. A turn-on position of the light emitting diodes in the first light source 742 may be changed by a controller 116 in accordance with the part of the eye 111 desired to be imaged. Light from the first light source 742 is guided to the eye 111 to be inspected by the dichroic filter 740 via the third lens 744. The light emitted from the first light source 742 is visible light and may have a wavelength of 520 nm.

An example of the WF-SLO 732 is illustrated in FIG. 7B. The WF-SLO 732 includes a second light source 746 or an input for receiving light from the second light source 746. The second light source 746 may be a laser, a lamp, a diode, a semiconductor laser, a super luminescent diode, a gas laser, a fiber coupled light source, a fiber based light source, some other suitable light source, or a set of light sources. The second light source 746 may be coherent or incoherent. In order to reduce the brightness as perceived by the subject while maintaining suitable resolution for fundus observation, a wavelength of the second light source 746 may be in the near infrared range of 700 nm to 1,000 nm. The wavelength of the second light source 746 may be non-visible light. In an embodiment, a semiconductor laser having a wavelength of 780 nm is used. Light emitted from the second light source 746 may be transmitted through a fiber to be emitted from a fiber collimator as a collimated beam (measuring light).

The measuring light passes through a first beam splitter 750 and a fourth lens 748-1 and is guided to a first scanner 109-4. The first scanner 109-4 may be a resonant scanner which scans the light along a first axis. The measuring light from the first scanner 109-4 may then pass through a fifth lens 748-3 and a sixth lens 748-4 which may focus the light onto a second scanner 109-5. The second scanner 109-5 may be a galvano scanner driven by a triangle signal or a saw tooth signal both of which are ramp signals along a second axis. Light from the second scanner is then transmitted via the ocular lens unit 730 to the subject 111. The ocular lens unit 730 gathers light from the subject 111 and guides back into the WF-SLO 732. The gathered light from the subject 111 that has been guided back to WF-SLO 732 by the combiner 738 is then sent back through the second scanner 109-5, the fifth lens 748-3 and the sixth lens 748-4, and the first scanner 109-4 before it hits the first beam splitter 750. The first beam splitter 750 guides a portion of the gathered light to a seventh lens 748-2 and to a first detector 752.

The first axis and the second axis are substantially orthogonal to each other. The first axis corresponds to a main scanning direction, and the second axis corresponds to a sub scanning direction.

The beam that has entered the eye 111 irradiates a fundus of the eye to inspect the subject 111 using the spot formed by the beam. This beam is reflected or scattered by the fundus of the eye 111 and follows the same optical path and is received by the first detector 752 which may be an avalanche photodiode (APD).

In an alternative embodiment, the second source 746 is a fiber coupled light source, the seventh lens 748-2 is GRIN lens that couples the fiber coupled light to the first detector 752, the first beam splitter 750 is a fused fiber coupler or a fiber coupled beam splitter, and the fourth lens 748-1 is a fiber coupled GRIN lens.

FIG. 7C is an illustration of an exemplary AO-SLO 734 which may be used in an embodiment. The AO-SLO 734 may use a third light source 101. The third light source 101 may be a SLD light source having a wavelength of 840 nm. The third light source 101 may be a non-visible light source or an infrared light source. The third light source 101 may have wavelength spectrum that is different from a wavelength spectrum of the second light source 746. The third light source 101 may be shared for imaging the fundus and for measuring a wavefront of the image. In an alternative embodiment, the wavefront may be measured with one wavelength while the fundus is imaged with a second different wavelength.

The light emitted from the third light source 101 may be transmitted through a fiber to be radiated via an eighth lens 103 or a fiber collimator as collimated measuring light. The embodiment may include the third light source 101 or include an input for the third light source 101. The radiated measuring light is transmitted through a second beam splitter 104 and guided to a compensation optical system.

The compensation optical system includes a third beam splitter 106, a wavefront sensor 115 for measuring aberration, a wavefront correction device 108, and mirrors 107-1 to 107-4 (first mirror 107-1; second mirror 107-2; third mirror 107-3; and fourth mirror 107-4) for guiding the light to those components. The mirrors 107-1 to 107-4 may be arranged such that the eye 111 to be inspected, the wavefront sensor 115, and the wavefront correction device 108 may have an optically conjugate relationship to each other. The wavefront correction device 108 may be a spatial phase modulator, such as a reflective liquid crystal element, a deformable mirror, or a translucent liquid crystal element.

The measuring light may enter the wavefront correction device 108 and may be emitted to the third mirror 107-3. Similarly, the light that has returned from the fundus of the eye 111, enters the wavefront correction device 108, and is then emitted to the second mirror 107-2. The measuring light is scanned two-dimensionally by a third scanner 109-1 which is then sent to a fourth scanner 109-2 via a ninth lens 754 and a tenth lens 756. The third scanner 109-1 may be a high-speed resonance scanner. The fourth scanner 109-2 may be a galvano scanner. The third scanner 109-1 and the fourth scanner 109-2 scan in directions that are in substantially orthogonal directions to each other. The third scanner 109-1 may scan along the first axis in the same manner as the first scanner 109-4. The third scanner 109-1 may scan along the x-axis. The fourth scanner 109-2 may scan along the y-axis.

The measuring light scanned by the third scanner 109-1 and the fourth scanner 109-2 is then transmitted via the ocular lens unit 730 to the subject 111. The ocular lens unit 730 gathers light from the subject 111 and guides it back into the AO-SLO 734. The gathered light from the subject 111 that has been guided back to AO-SLO 734 by the combiner 738 is then sent back through the fourth scanner 109-2, the ninth lens 754 and the tenth lens 756, the third scanner 109-1, mirror 107-4, mirror 107-3, wavefront correction device 108, mirror 107-2, and mirror 107-1, before it hits the third beam splitter 106. The third beam splitter 106 guides a portion of the gathered light to the wavefront sensor 115. The third beam splitter 106 guides another portion of the gathered light to a second beam splitter 104. The second beam splitter 104 guides the gathered light to an eleventh lens 112 and to a second detector 114.

The measuring light that has entered the eye 111 to be inspected has been reflected or scattered by the fundus and follows the same optical path as the measurement light. The wavefront sensor 115 measures a wavefront of the beam from the fundus. The wavefront sensor 115 may be a Shack-Hartmann sensor, a pyramid wavefront sensor, or some other method for characterizing a wavefront. The detector 114 may be a photomultiplier tube. The detector 114 may be a fiber coupled detector and the lens 112 may be a fiber collimator. In an alternative embodiment, the second beam splitter 104 may be a partially silvered prism.

In an alternative embodiment, the third source 101 is a fiber coupled light source or is coupled to a fiber via the eighth lens 103, the eleventh lens 112 is a GRIN lens that couples the fiber coupled light to the second detector 114, the second beam splitter 104 is a fused fiber coupler or a fiber coupled beam splitter, and is collimated by a fiber coupled GRIN lens.

The first detector 752 converts light into an electrical signal which is then converted into a wide field image of a portion the fundus Ea. The second detector 114 converts light into an electrical signal which is then converted into a narrow field image of a narrower portion of the fundus.

The wavefront sensor 115 and the wavefront correction device 108 are connected to each other. One or more processors associated with the controller 116 and/or the PC 117 may be used to calculate a modulation amount of the wavefront correction device 108 which is calculated based on information from the wavefront sensor 115. The wavefront sensor 115 and the wavefront correction device 108 may form a closed loop feedback system.

Figure 7D:
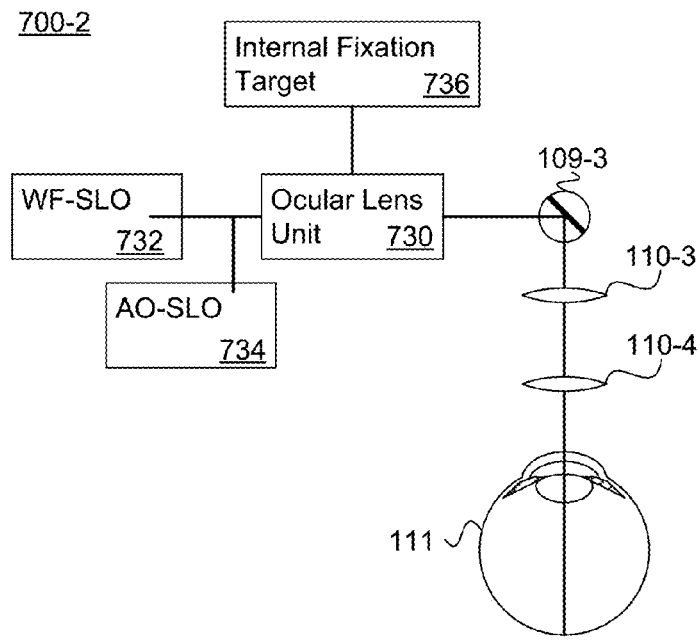

FIG. 7D is an illustration of an embodiment 700-2 substantially similar to embodiment 700-1 and also includes an additional tracking mirror 109-3. The embodiment 700-2 may also include an optional relay lenses 110-3 and 110-4. The tracking mirror 109-3 may consist of 2 scanners or one 2-dimensional scanner. The tracking mirror 109-3 is moved to compensate for detected movements of the subject 111, such that the fundus stays in focus and within the field of view. In an alternative embodiment, there is no tracking mirror and the scanning mirrors 109-4, 109-5, 109-1, and 109-2 are moved to compensate for the detected movements of the subject 111, such that the fundus stays in focus and within the field of view. In other embodiments, there may be additional tracking mirrors to compensate for the detected movements of the subject 111 in addition to the scanning mirrors 109-4, 109-5, 109-1, and 109-2.

An alternative embodiment, may include multiple different tip-tilt mirrors or two sets of single axis mirrors may be used in concert for optical stabilization. A coarse tip-tilt mirror may be used for coarse optical stabilization. A fine tip-tilt mirror may be used for fine optical stabilization. One or both of the tip-tilt mirrors may be replaced with two single axis rotating mirrors.

Figure 8A:
FIGS. 8A-B are illustrations of reference images that may be implemented used in an embodiment.
Figure 8B:
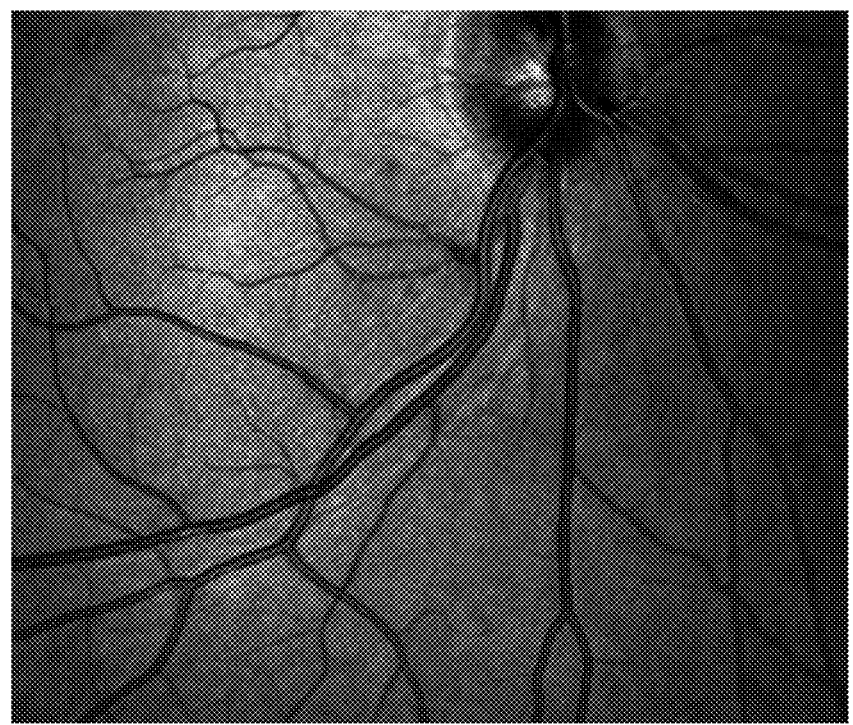

In an integrated ophthalmoscope such as 700-1 or 700-2 where a WF-SLO 732 and an AO-SLO 734 do eye tracking concurrently, it may be possible to lock a steering mirror such as 109-3 or its equivalent to the same retinal area from the WF-SLO 732 from the same subject 111. This feature may require the WF-SLO 732 to use the same reference image for all imaging sessions. The applicants have noted that images produced by the WF-SLO 732 typically have less intra-image distortion than images produced by the AO-SLO 734. different reference images produced by the WF-SLO 732 may be pre-recorded from imaging sessions at different retinal locations. FIG. 8A is an illustration of a reference image 804-c1 that may be produced by the WF-SLO 732. A particular reference image 804-c1 may be chosen by an operator or automatically picked from a sequence of images. An alternative reference image 804-c2 as illustrated in FIG. 8B may be produced by averaging multiple images.

Different reference images at different retinal locations on the subject 111 may be stored in volatile memory or non-volatile memory such as a hard drive or a flash drive. The reference images may be stored, on the ophthalmoscope, a locally connected computer, or a storage device that is accessed via a network. One of the reference images may be loaded from a storage location and into a local memory used by an embodiment that performs eye tracking. The eye tracking may be performed by tracking software. The reference image may be loaded into memory before the eye tracking software is launched. A different reference image from a different retinal area may be loaded into the tracking software when the imaging area is moved to a different retinal area.

First Alternative Automatic Reference Image Selection Method

Figure 9:
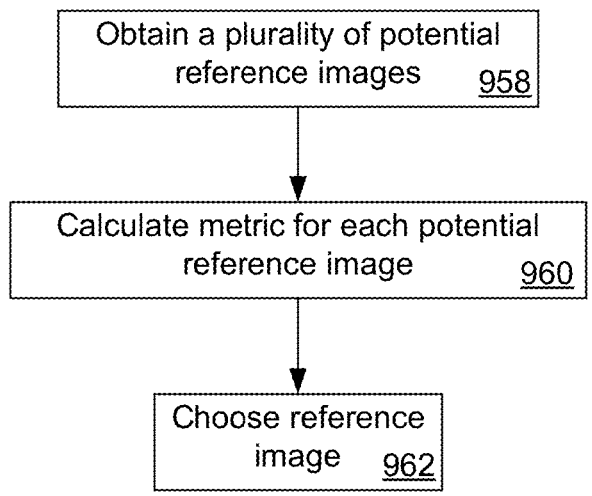
FIG. 9 is an illustration of a method that may be implemented in an embodiment.

FIG. 9 is an illustration of a method 900 for choosing a reference image. A first step 958 may include obtaining a plurality of potential reference images. A second step 960 may include calculating a metric based on a signal strength associated with each of the potential reference images. The metric may include the average intensity of each potential reference image. A third step 962 may include choosing the reference image based on the metric of each potential reference image. For example, the particular reference image may be chosen when the metric for the particular reference image is in a range of values. The metric may also be based on identifying a particular image structure within the image. Examples, of particular image structures, may include the clear appearance of branches of vessels, thick vessels, or optic nerve heads.

The tracking method may use reference images that were pre-recorded at an earlier date. The AO-SLO and the WF-SLO may use different tracking methods.

Controller

Figure 10:
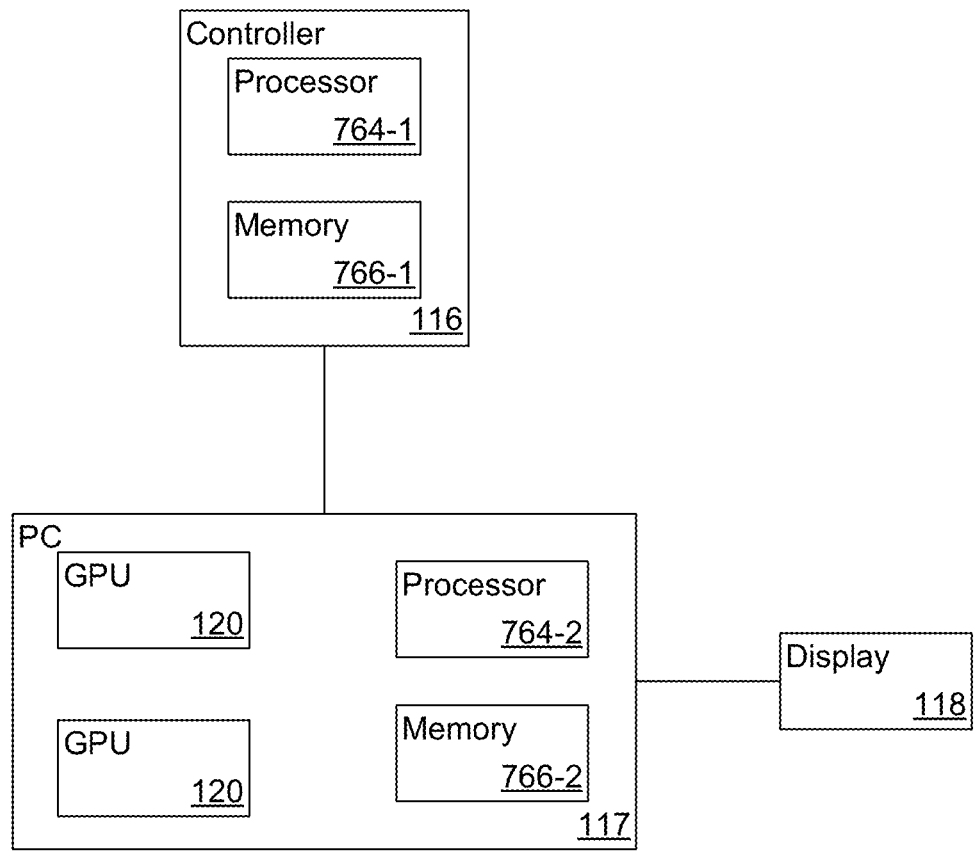
FIG. 10 is an illustration of a controller that may be used in an embodiment.

FIG. 10 is an illustration of the PC 116 and controller 117 that may be used in an embodiment. The controller 116 receives input signals and outputs control signals. The controller 116 may be a general purpose computer, a device specifically designed to control the ophthalmoscope or measuring instrument, or a hybrid device that uses some custom electronics along with a general purpose computer 117. The input signals and control signals may be digital signals and/or analog signals. The controller 116 may include an analog to digital converter (ADC) and a digital to analog converter (DAC). The input signals may include one more signals such as a signal from the wavefront sensor 115, a signal from the detector 114, and one or more signals from one or more other sensors. The control signals may include a first control signal to a wavefront adjustment device 108 and signals to one or more of the scanners 109-1, 109-2, and/or 109-3. The control signals may include additional signals to other components of the instrument.

The controller 116 includes a processor 764-1. The processor 764-1 may be a microprocessor, a CPU, an ASIC, a DSP, and/or a FPGA. The processor 764-1 may refer to one or more processors that act together to obtain a desired result. The controller 116 may include a memory 766-1. The memory 766-1 may store calibration information. The memory 766-1 may also store software for controlling the ophthalmoscope. The memory 766-1 may be a form of a non-transitory computer readable storage medium. The non-transitory computer readable storage medium may include, for example, one or more of a hard disk, a random-access memory (RAM), a read only memory (ROM), a distributed storage system, an optical disk (CD, DVD or Blu-Ray Disc, a flash memory device, a memory card, an internet connected storage device, an intranet connected storage device, or the like.

The controller 116 may be connected to a computer (PC) 117 via a direct connection, a bus, or via a network. The computer 117 may include input devices such as a keyboard, a mouse, and/or a touch screen. The controller 116 may include input devices such as a keyboard, a mouse, a touch screen, knobs, switches, and/or buttons. The computer 117 may be connected to a display 118. The results of the ophthalmoscope may be presented to a user via the display 118. The tracking software which may be used to implement an embodiment that may perform calculations on the controller 116 independently of the PC 117 or with the help of the PC 117. The PC 117 may include a processor 764-2, a memory 766-2. The PC 117 may also include one or more GPUs 120. The image correlation calculations may be performed on the one or more GPUs 120.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. A method of imaging a scanning area of a subject by scanning imaging light over periods of time on the scanning area of the subject, the method comprising:
   constructing a plurality of images based on detection of the imaging light from the scanning area of the subject, each image among the plurality of images obtained during a different time period;
   wherein the plurality of images includes at least: a reference image, a first image, and a second image;
   wherein the first image is obtained during a first period of time, the second image is obtained during a second period of time, the reference image is obtained during a third period of time that is prior to the first period of time and the second period of time;
   estimating a first relative change in position of the scanning area of the subject by comparing the reference image and the first image;
   estimating a second relative change in position of the scanning area of the subject by comparing the reference image and the second image;
   estimating a third relative change in position of the scanning area of the subject by comparing the first image and the second image;
   calculating a quality metric of estimation of the second relative change in position based on: the first relative change in position; the second relative change in position; the third relative change in position; and
   comparing the quality metric to a threshold,
      in a first case wherein the quality metric is less than the threshold, adjusting position of the scanning area based on the second relative change in position; and
      in a second case wherein the quality metric is not less than the threshold, obtaining a new second image during a new second period of time.

2. The method of claim 1, wherein in the second case, the position of the scanning area is controlled based upon previous image position information.

3. The method of claim 1, wherein the second image is an image of the scanning area of the subject that is obtained immediately after the first image is obtained.

4. The method of claim 1, further comprising in the first case:
   setting the second image as a new first image;
   setting the second relative change in position as a new first relative change in position;
   obtaining the new second image during the new second period of time, wherein the new second image is an image of the scanning area of the subject that is obtained immediately after the new first image is obtained;

estimating a new second relative change in position of the scanning area of the subject by comparing the reference image and the new second image;

estimating a new third relative change in position of the scanning area of the subject by comparing the new first image and the new second image;

calculating a new quality metric of estimation of the new second relative change in position based on: the new first relative change in position; the new second relative change in position; the new third relative change in position; and comparing the new quality metric to the threshold,
in the first case wherein the new quality metric is less than the threshold, adjusting position of the scanning area based on the new second relative change in position; and
in the second case wherein the new quality metric is greater than the threshold, reobtaining the new second image during a reset new second period of time.

5. The method of claim 1 further comprising:
performing pre-processing on each of the plurality of images before estimating relative changes in position; and
wherein the pre-processing is changed according to status of imaging.

6. The method of claim 5, wherein the pre-processing includes applying either a smoothing filter or a Sobel filter according to status of imaging.

7. The method of claim 5 wherein the status of imaging is an average intensity of an image among the plurality of images to the pre-processing is to be applied.

8. The method of claim 5 wherein the status of imaging is a size of the scanning area.

9. The method of claim 5, wherein the status of imaging is a focusing position of the imaging light.

10. The method of claim 5, wherein pre-processing includes dividing each of the plurality of images into smaller images, the estimating of relative changes in position is performed on the smaller images, and adjusting the position of the scanning area, are all done during periods of time in which each undivided image is being obtained.

11. The method of claim 1, further comprising:
calculating a second quality metric based on a magnitude of the second relative change in position;
comparing the second quality metric to a second threshold,
in a third case wherein the second quality metric is less than the second threshold, adjusting position of the scanning area based on the second relative change in position; and
in a second case wherein the second quality metric is not less than the second threshold, not adjusting the position of the scanning area.

12. The method of claim 1 further comprising:
obtaining a plurality of potential reference images; and
setting the reference image as an average of the plurality of potential reference images.

13. The method of claim 1 further comprising:
obtaining a plurality of potential reference images; and
setting one of the plurality of potential reference images as the reference image based on imaging conditions of each of the plurality of potential reference images.

14. The method of claim 13, wherein the imaging condition is an average intensity of each of the plurality of potential reference images.

15. The method of claim 13, wherein the imaging condition is a similarity between a first potential reference image and a second potential reference image obtained immediately prior to obtaining the first potential reference image.

16. The method of claim 1 wherein,
in the first case, the second image is used to construct a larger image by stitching the second image together with other images, and
in the second case, the second image is not used to construct the larger image.

17. The method of claim 1 wherein,
in the first case, the second image is used to create a video image by using the second image together with other images to form a time series, and
in the second case, the second image is not used to construct the video image.

18. The method of claim 1, wherein:
first image and the second image are among a time series of images of the scanning area of the subject; and
the second image is the next image after the first image in the time series of images of the scanning area of the subject.

19. A non-transitory computer readable medium encoded with instructions for a processor to perform the method of claim 1.

20. A controller for controlling an apparatus for imaging a scanning area of a subject by scanning imaging light over periods of time on the scanning area of the subject, comprising:
a processor including one or more processing components;
a memory;
wherein the processor constructs a plurality of images based on detection of the imaging light from the scanning area of the subject, each image among the plurality of images obtained during a different time period;
wherein the plurality of images includes at least: a reference image, a first image, and a second image;
wherein the first image is obtained during a first period of time, the second image is obtained during a second period of time, the reference image is obtained during a third period of time that is prior to the first period of time and the second period of time;
wherein the processor estimates a first relative change in position of the scanning area of the subject by comparing the reference image and the first image;
wherein the processor estimates a second relative change in position of the scanning area of the subject by comparing the reference image and the second image;
wherein the processor estimates a third relative change in position of the scanning area of the subject by comparing the first image and the second image;
wherein the processor calculates a quality metric of estimation of the second relative change in position based on: the first relative change in position; the second relative change in position; the third relative change in position; and
wherein the processor compares the quality metric to a threshold,
in a first case wherein the quality metric is less than the threshold, adjusting position of the scanning area based on the second relative change in position; and in a second case wherein the quality metric is not less than the threshold, obtaining a new second image during a new second period of time.

* * * * *